US012751766B2

(12) United States Patent
Zhong et al.

(10) Patent No.: US 12,751,766 B2
(45) Date of Patent: Oct. 6, 2026

(54) COMPOSITIONS AND METHODS FOR LASER LITHOTRIPSY USING NANOPARTICLE FINE-TUNED NIR ABSORPTION

(71) Applicants: Duke University, Durham, NC (US); The University of Chicago, Chicago, IL (US)

(72) Inventors: Pei Zhong, Durham, NC (US); Qingsong Fan, Chicago, IL (US); Po-Chun Hsu, Durham, NC (US); Christine Payne, Durham, NC (US); Michael Lipkin, Durham, NC (US)

(73) Assignees: Duke University, Durham, NC (US); The University of Chicago, Chicago, IL (US)

( * ) Notice: Subject to any disclaimer, the term of this patent is extended or adjusted under 35 U.S.C. 154(b) by 134 days.

(21) Appl. No.: 18/962,953

(22) Filed: Nov. 27, 2024

(65) Prior Publication Data

US 2025/0169882 A1 May 29, 2025

Related U.S. Application Data

(60) Provisional application No. 63/602,711, filed on Nov. 27, 2023.

(51) Int. Cl.
*A61K 41/00* (2020.01)
*A61B 18/24* (2006.01)
(Continued)

(52) U.S. Cl.
CPC ........ *A61B 18/245* (2013.01); *A61K 41/0028* (2013.01); *A61K 47/02* (2013.01);
(Continued)

(58) Field of Classification Search
CPC .................. A61B 18/245; A61B 18/26; A61B 2017/22085; A61B 2018/00577;
(Continued)

(56) References Cited

U.S. PATENT DOCUMENTS

2021/0236524 A1 8/2021 Laser et al.

FOREIGN PATENT DOCUMENTS

WO 2021222572 A1 4/2020

OTHER PUBLICATIONS

Pishchalnikov Y, Behnke-Parks W, Stoller M. V05-12 Diminishing Fragmentation of Stones With Subsequent Pulses in Laser Lithotripsy. Journal of Urology, Sep. 1, 2021; 206(Supplement 3):e389.
(Continued)

*Primary Examiner* — Scott Luan
(74) *Attorney, Agent, or Firm* — Casimir Jones, S.C.; Thomas J. Lyneis

(57) ABSTRACT

Systems and methods for performing laser lithotripsy include introducing a lithotripsy medium containing nanoparticles into a body cavity comprising target obstructions and applying laser energy through the lithotripsy medium to disrupt the target obstructions. The nanoparticles may have diameters configured to enhance absorption efficiency of the laser energy. The nanoparticles may include organic polymers such as PEDOT: PSS or inorganic compounds such as indium tin oxide. Systems may include a laser source, a fluid delivery component configured to deliver the nanoparticle-containing lithotripsy medium, and an optical fiber for delivering laser energy. Methods of manufacturing lithotripsy media include selecting target wavelengths, synthesizing nanoparticles with corresponding absorption characteristics, and dispersing the nanoparticles at selected concentrations.

40 Claims, 18 Drawing Sheets

(51) Int. Cl.
*A61K 47/02* (2006.01)
*A61K 47/34* (2017.01)
*A61B 17/22* (2006.01)
*A61B 18/00* (2006.01)

(52) U.S. Cl.
CPC .... *A61K 47/34* (2013.01); *A61B 2017/22085* (2013.01); *A61B 2018/00577* (2013.01); *A61B 2018/00702* (2013.01)

(58) Field of Classification Search
CPC ...... A61B 2018/00702; A61K 41/0028; A61K 47/02; A61K 47/03
See application file for complete search history.

(56) References Cited

OTHER PUBLICATIONS

Hyams, E. S. & Matlaga, B. R. Economic impact of urinary stones. Transl Androl Urol 3, 278-283 (2014).
Scales, C. D., Smith, A. C., Hanley, J. M., Saigal, C. S., & Urologic Diseases in America Project. Prevalence of kidney stones in the United States. Eur Urol 62, 160-165 (2012).
Weiss, B., Shah, O. Evaluation of dusting versus basketing—can new technologies improve stone-free rates?. Nat Rev Urol 13, 726-733 (2016).
Pietropaolo A, Schembri M, Somani BK. Dusting and pop-dusting for kidney stone disease: Video and outcomes. Turk J Urol. May 21, 2020;46(4):326-7.

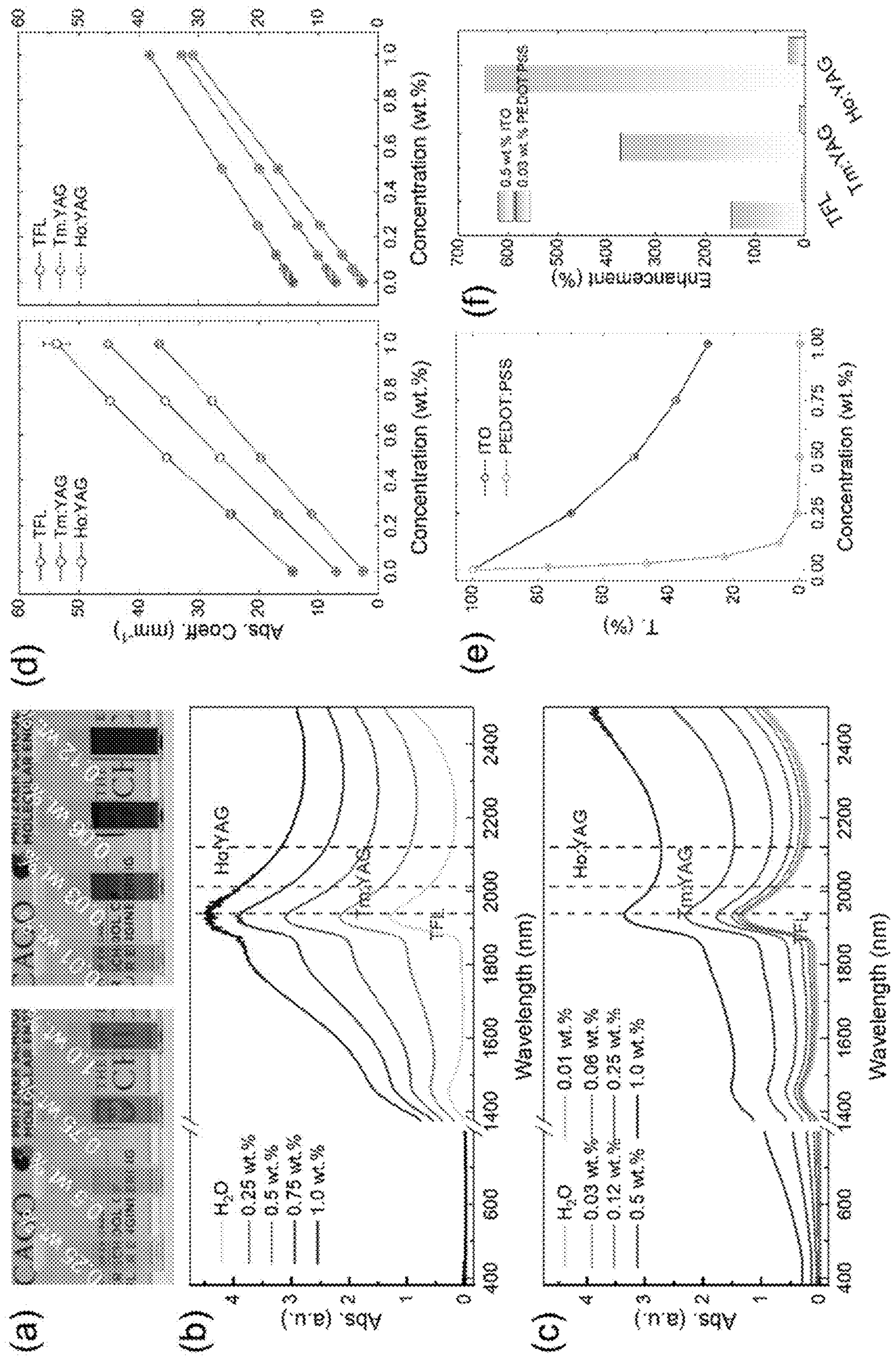
FIG. 15A-F

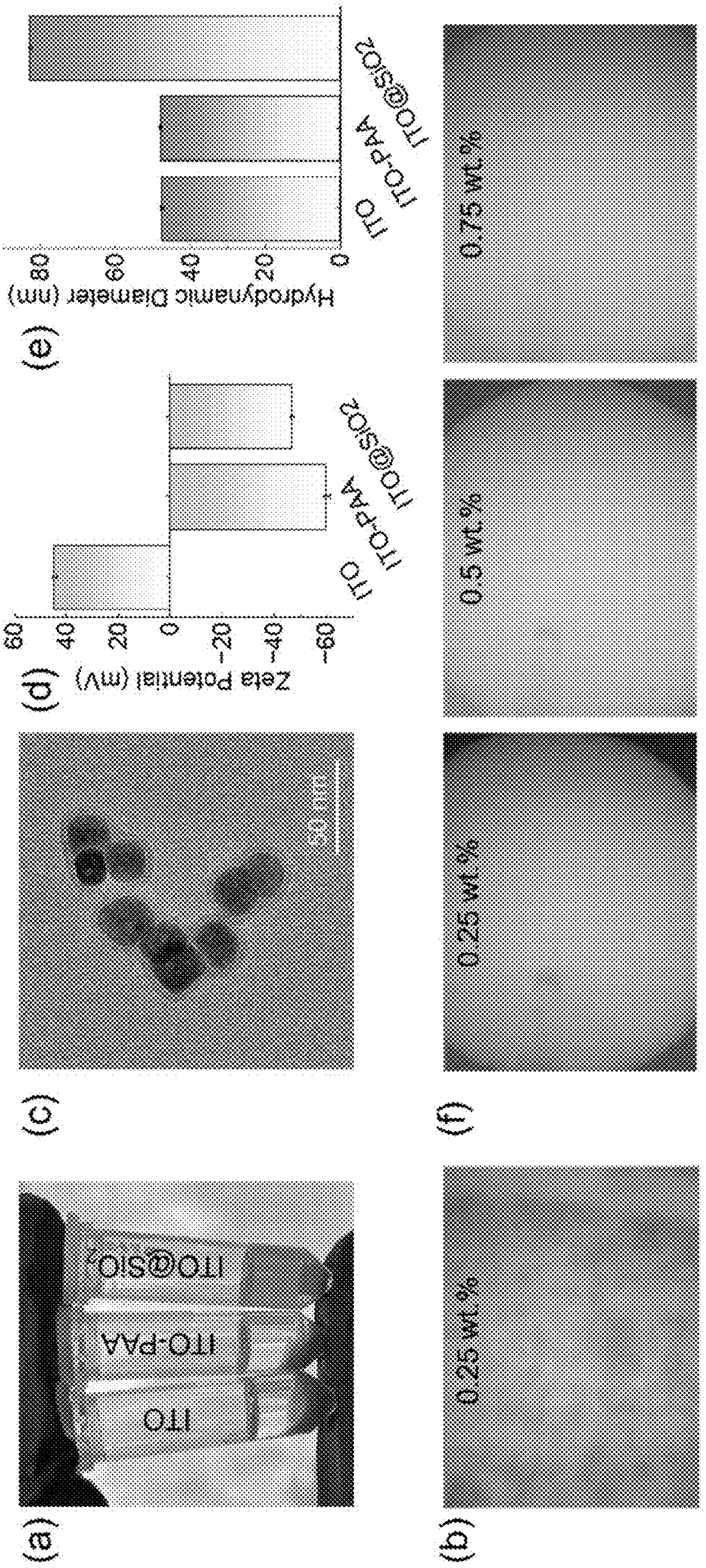
FIG. 16A-F

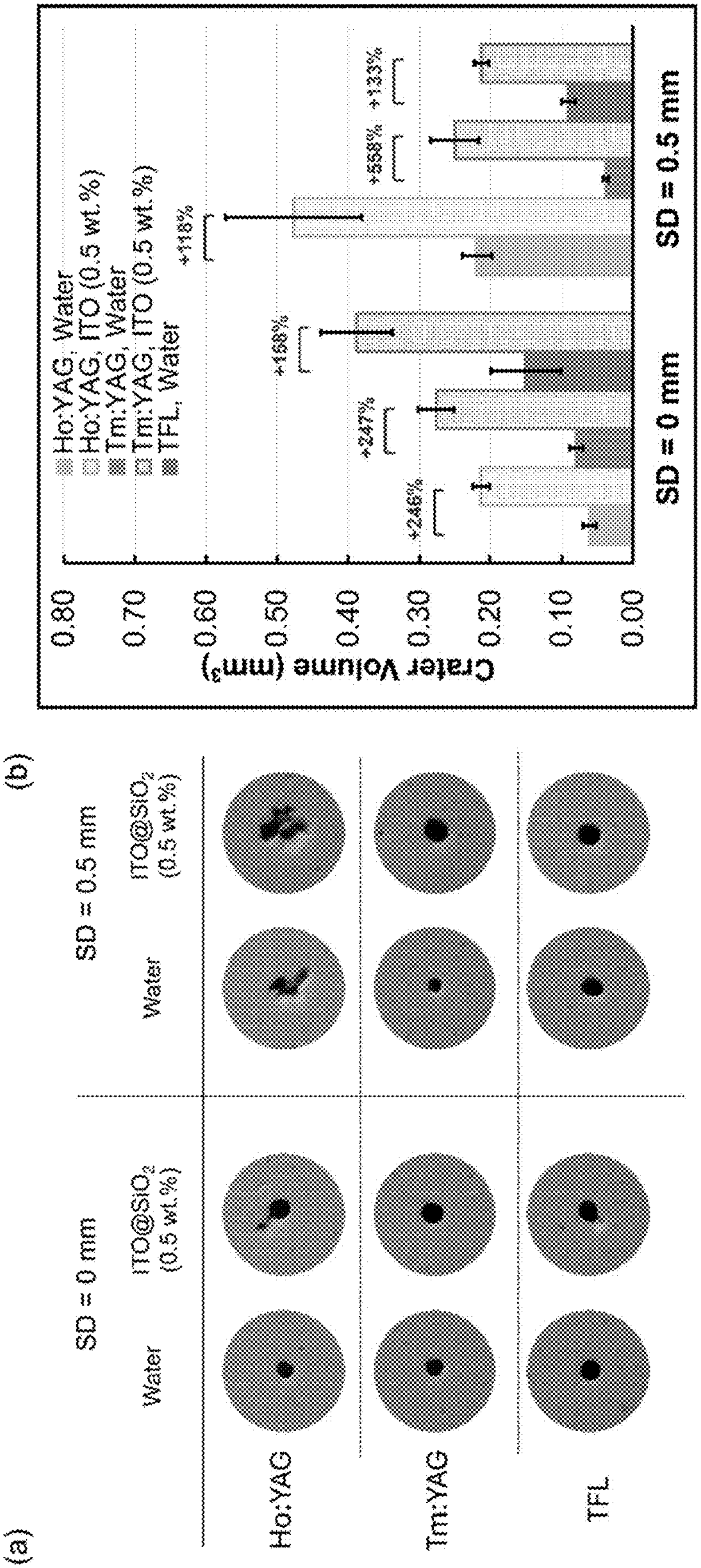
FIG. 17A-B

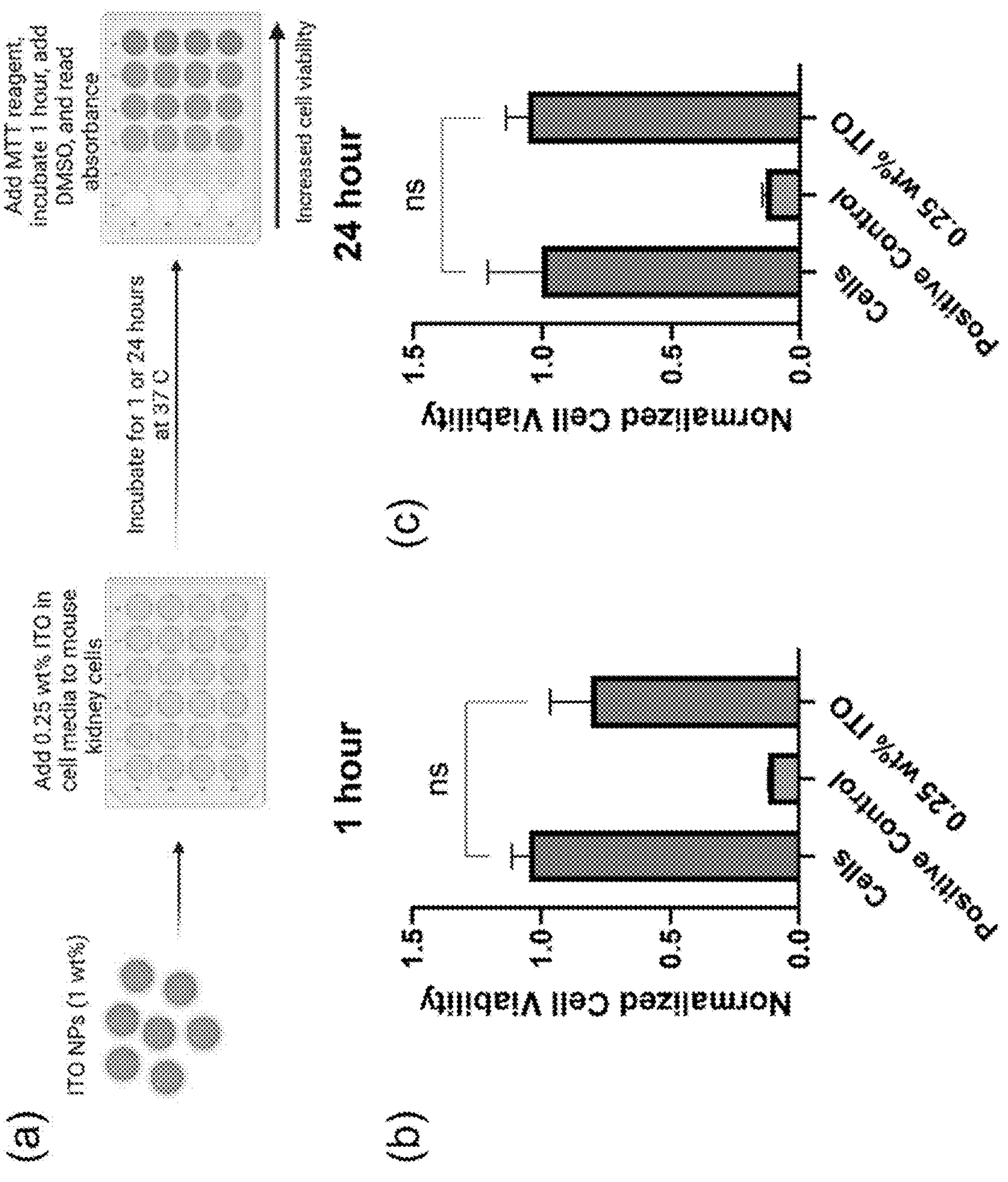
FIG. 18A-C

COMPOSITIONS AND METHODS FOR LASER LITHOTRIPSY USING NANOPARTICLE FINE-TUNED NIR ABSORPTION

CROSS-REFERENCE TO RELATED APPLICATIONS

The present application claims priority to U.S. Provisional Application No. 63/602,711, filed Nov. 27, 2023, which is incorporated herein by reference in its entirety.

GOVERNMENT FUNDING

This invention was made with Government support under Federal Grant nos. 5P20 DK123970, 2R01DK052985, and 1P20-DK135107-01 awarded by the National Institutes of Health. The Federal Government has certain rights to this invention.

FIELD

The present invention generally relates to medical devices and procedures, and more particularly to systems and methods for performing laser lithotripsy procedures. Specifically, the invention relates to enhanced laser lithotripsy techniques utilizing nanoparticle-containing media to improve the efficiency of stone fragmentation during urological procedures.

The invention further relates to the field of medical fluid delivery systems, particularly those incorporating engineered nanoparticles for optimizing laser energy absorption during surgical procedures. Additionally, the invention pertains to methods of manufacturing specialized lithotripsy media with tailored optical properties for use in laser-based stone removal procedures.

BACKGROUND

Urinary stone disease (USD) is a benign yet severely painful genitourinary condition affecting nearly 1 in 10 Americans. In 2000, the annual health expenditure for USD in the U.S. exceeded $2 billion, which continues to rise rapidly today. For USD patients, minerals such as calcium oxalate, calcium phosphate, and uric acid gradually crystallize and form large stones that cannot be naturally expelled from the urinary system. When these stones grow to a size capable of obstructing urine flow, they cause intense pain along with additional symptoms like frequent urination, difficulty urinating, and blood in the urine. Various techniques have been developed to remove urinary stones, including extracorporeal shock wave lithotripsy, laser lithotripsy (LL) via ureteroscopy, and percutaneous nephrolithotomy.

LL represents the most rapidly growing intervention method for USD treatment. While extracorporeal shock wave lithotripsy offers advantages of non-invasiveness and anesthesia-free treatment, it exhibits lower efficacy in managing large (>1 cm) or hard stones, resulting in reduced clearance and stone-free rates. In contrast, LL has made significant advancements, particularly those utilizing the holmium: yttrium-aluminum-garnet (Ho:YAG) laser, which has the suitable pulse duration, repetition frequency, and peak power to offer numerous advantages, such as efficacy in fragmenting all types of stones, minimal retropulsion, and compatibility with low-cost flexible optical fibers. Notably, large series of clinical studies have shown that Ho:YAG LL is safe in children, in all stages of pregnancy, and in patients with bleeding disorders. Ho:YAG LL has established itself as the gold standard in USD management.

Research and clinical practice of Ho:YAG LL over the past two decades have pursued the goal of maximizing stone ablation efficiency with minimal thermal injury. From the optical science perspective, this effort can be facilitated by controlling the light-matter interaction, particularly through modulating the absorption coefficient (FIG. 1). Previous research efforts have focused primarily on manipulating the laser output profile, including pulse energy, pulse duration, and frequency. These approaches did not change the fundamental physical properties of water and stone at the wavelength of Ho:YAG (2=2120 nm), limiting the accessible parameter space and enhancement potential. Studies exploring stone treatment with laser-absorbing pigments or nanoparticles for augmenting stone damage in vitro faced challenges in clinical translation and maintaining efficacy after surface ablation. Research has shown that vapor bubble collapse at the fiber tip plays a critical role in stone dusting during LL, highlighting the importance of considering both the stone and surrounding fluid environment.

The use of nanoparticle dispersion (nanofluid) shows promise in enhancing laser energy absorption and ablation efficiency of Ho:YAG LL. Research utilizing poly(3,4-ethylenedioxythiophene) polystyrene sulfonate (PEDOT: PSS) nanoparticles, a well-established polymeric material known for its absorption peak in the near-infrared spectrum, demonstrates significant improvements. LL conducted in a 0.03 wt. % PEDOT: PSS nanofluid showed an improvement of 38-727% in stone ablation compared to procedures conducted in water at the fiber tip-to-stone standoff distance (SD) of 0-1 mm. Analysis of bubble dynamics and stone laser absorptivity after soaking indicates that both accelerated and amplified vapor bubble expansion and collapse, as well as enhanced absorption of laser energy by fluid trapped within the stones, contribute to the improved ablation efficiency.

There remains a need for improved systems and methods for performing laser lithotripsy procedures that can enhance treatment efficiency while maintaining safety. Particularly desirable are approaches that can be readily integrated with existing laser lithotripsy equipment and techniques.

SUMMARY

The present disclosure provides, in at least one aspect, methods of performing laser lithotripsy, the method comprising introducing a lithotripsy medium comprising nanoparticles into a body cavity of a subject, wherein the body cavity of the subject comprises one or more target obstructions, and applying laser energy through the lithotripsy medium to disrupt the one or more target obstructions, wherein the nanoparticles have a diameter configured to enhance absorption efficiency of the laser energy.

In some embodiments, the laser energy comprises a wavelength configured to enhance absorption efficiency of the laser energy by the lithotripsy medium.

In some embodiments, the wavelength of the laser energy is from about 750 nm to about 2500 nm.

In some embodiments, the diameter of the nanoparticles is from about 1 nm to about 250 nm.

In some embodiments, the nanoparticles are present in the lithotripsy medium at a concentration from about 0.001 wt. % to about 10 wt. %.

In some embodiments, the nanoparticles are comprised of at least one organic polymer.

In some embodiments, the at least one organic polymer comprises poly(3,4-ethylenedioxythiophene) polystyrene sulfonate (PEDOT: PSS).

In some embodiments, the wavelength of the laser energy is from about 1800 nm to about 2200 nm.

In some embodiments, the diameter of the nanoparticles is from about 50 nm to about 250 nm.

In some embodiments, the nanoparticles are present in the lithotripsy medium at a concentration from about 0.006 wt. % to about 0.03 wt. %.

In some embodiments, the laser energy is applied using a holmium laser.

In some embodiments, the nanoparticles are comprised of at least one inorganic compound.

In some embodiments, the at least one inorganic compound comprises indium tin oxide.

In some embodiments, the wavelength of the laser energy is from about 1800 nm to about 2200 nm.

In some embodiments, the diameter of the nanoparticles is from about 1 nm to about 100 nm.

In some embodiments, wherein the nanoparticles are present in the lithotripsy medium at a concentration from about 0.1 wt. % to about 1 wt. %.

In some embodiments, the laser energy is applied using a thulium laser.

In some embodiments, applying the laser energy comprises generating vapor bubbles in the lithotripsy medium between a laser fiber tip and the one or more target obstructions.

In some embodiments, the one or more target obstructions comprise kidney stones.

In some embodiments, the method further comprises providing at least a second lithotripsy medium comprising nanoparticles having a different diameter than the nanoparticles in the first lithotripsy medium, and alternating between the first and second lithotripsy mediums during the laser lithotripsy procedure to modify light absorption characteristics and/or efficiency.

In some embodiments, the first lithotripsy medium provides enhanced absorption efficiency at a first wavelength and the second lithotripsy medium provides enhanced absorption efficiency at a second wavelength.

The present disclosure provides, in at least another aspect, systems for performing laser lithotripsy, comprising a laser source configured to generate laser energy, a fluid delivery component configured to deliver a lithotripsy medium comprising nanoparticles having a diameter selected to enhance absorption efficiency at the wavelength of the laser energy, and an optical fiber configured to deliver the laser energy to one or more target obstructions through the lithotripsy medium.

In some embodiments, the laser energy comprises a wavelength configured to enhance absorption efficiency of the laser energy by the lithotripsy medium.

In some embodiments, the wavelength of the laser energy is from about 750 nm to about 2500 nm.

In some embodiments, the diameter of the nanoparticles is from about 1 nm to about 250 nm.

In some embodiments, the nanoparticles are present in the lithotripsy medium at a concentration from about 0.001 wt. % to about 10 wt. %.

In some embodiments, the nanoparticles are comprised of at least one organic polymer.

In some embodiments, the at least one organic polymer comprises poly(3,4-ethylenedioxythiophene) polystyrene sulfonate (PEDOT: PSS).

In some embodiments, the wavelength of the laser energy is from about 1800 nm to about 2200 nm.

In some embodiments, the diameter of the nanoparticles is from about 50 nm to about 250 nm.

In some embodiments, the nanoparticles are present in the lithotripsy medium at a concentration from about 0.006 wt. % to about 0.03 wt. %.

In some embodiments, the laser source is a holmium laser.

In some embodiments, the nanoparticles are comprised of at least one inorganic compound.

In some embodiments, the at least one inorganic compound comprises indium tin oxide.

In some embodiments, the wavelength of the laser energy is from about 1800 nm to about 2200 nm.

In some embodiments, the diameter of the nanoparticles is from about 1 nm to about 100 nm.

In some embodiments, the nanoparticles are present in the lithotripsy medium at a concentration from about 0.1 wt. % to about 1 wt. %.

In some embodiments, the laser source is a thulium laser.

In some embodiments, the fluid delivery component is configured to deliver a second lithotripsy medium comprising nanoparticles having a second diameter selected to modify light absorption characteristics and/or efficiency.

The present disclosure provides, in at least yet another aspect, methods of manufacturing a lithotripsy medium, comprising selecting a target wavelength for enhanced absorption of laser energy, synthesizing nanoparticles having a diameter selected to provide an absorption peak at the target wavelength, and dispersing the nanoparticles in the lithotripsy medium at a selected concentration.

BRIEF DESCRIPTION OF THE DRAWINGS

The accompanying Figures and Example are provided by way of illustration and not by way of limitation. The foregoing aspects and other features of the disclosure are explained in the following description, taken in connection with the accompanying example figures (also "FIG.") relating to one or more embodiments in accordance with the present disclosure.

PSS nanofluids at various standoff distances (SDs) when the fiber tip was placed beyond the scope end with an offset distance (OSD) of 3 mm. (c) Dimensional measurements of craters by optical coherence tomography (OCT) with an OSD of 3 mm. (d) Bubble collapse induced damage, which was obtained by the difference of damages in the long and short OSDs. (e) Photos and (f) dimensional measurements of craters produced on the Bego Stones with an OSD=0.25 mm. The values and error bars are the average results and standard deviations of 5 independent experiments under each condition. Significance of the volume measurements in (c) and (f) was calculated using Student's test. * $p<0.1$,  $p<0.01$, * $p<0.001$, **** $p<0.0001$, ns—not significant comparison are not presented.

FIG. 4A-D: Optical properties of PEDOT: PSS nanofluid. (a) Absorbance spectra of water and PEDOT: PSS nanofluids of different concentrations within the NIR range (path length of measurements: 0.2 mm). (b) The absorbance and derived penetration depth values at the wavelength of 2120 nm of PEDOT: PSS nanofluids. (c) Transmittance of PEDOT: PSS nanofluids in the visible spectrum (path length of measurements: 5 mm). (d) The calculated average transmittance over a wavelength range of 380-750 nm (inset: a digital photo of PEDOT: PSS nanofluids at different concentrations in cuvettes with a 5 mm path length).

Figure 5:
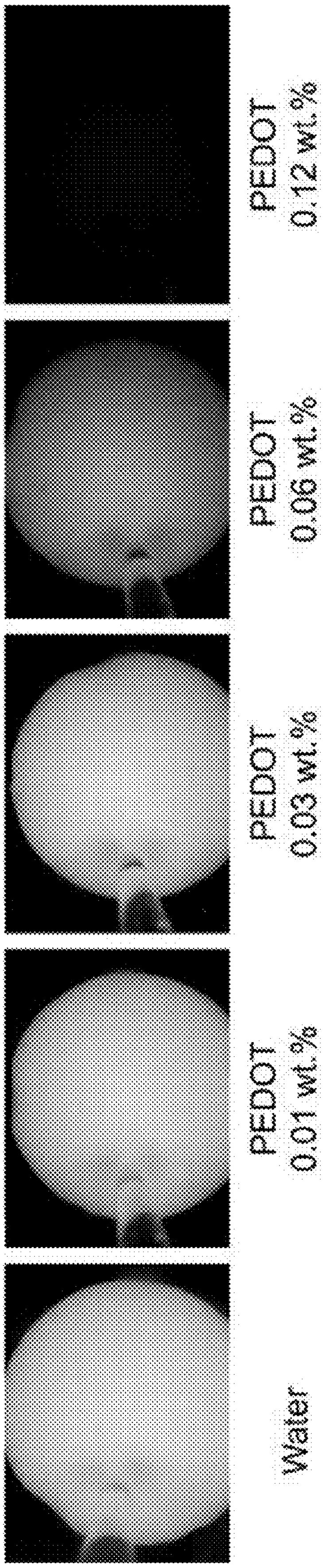

FIG. 5: The appearance of the BegoStone under ureteroscope in PEDOT: PSS solutions with different concentrations. The offset distance was set to 5 mm in the visibility test and there was an additional 2 mm set for the SD, so the distance between the ureteroscope and the stone surface in the images below was 7 mm in total. The edge of the stone starts to be blurry at the concentration of 0.06 wt. % and it becomes totally indistinguishable when the concentration further increases into 0.12 wt. %.

Figure 6:
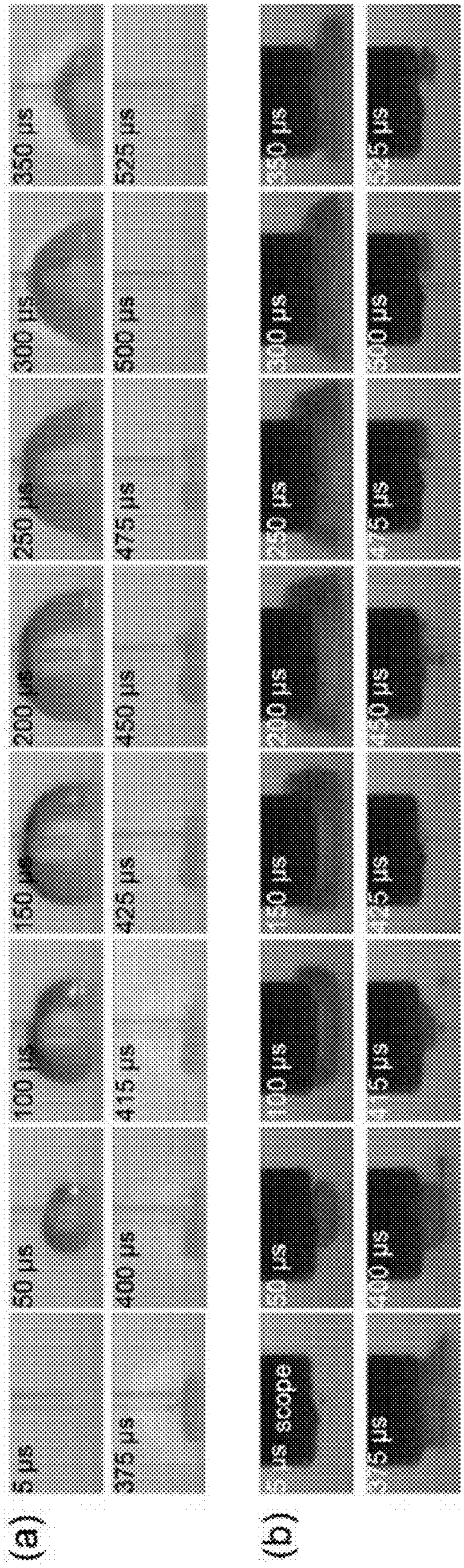

FIG. 6A-B: The bubble collapse behavior in a large OD (a, OD=3 mm) and a small OD (b, OD=0.25 mm). Both experiments had a glass slide placed in front of the fiber tip with a SD of 0.5 mm. The bubble collapse behaviors are dramatically different when ureteroscope were set at different distances (offset distance), which is illustrated in FIG. 6. In both cases of a large and a small OD (3 mm vs. 0.25 mm), a vapor bubble was quickly generated once the laser was turned on. However, the bubbles collapsed at different locations when the laser was turned off. The collapse occurred on the glass slide in the case of a large OD, while the bubble collapsed on the scope for a small OD scenario. This demonstrated that by moving the scope closer to the fiber tip, one can eliminate the cavitation induced ablation on the Bego stone.

Figure 7:
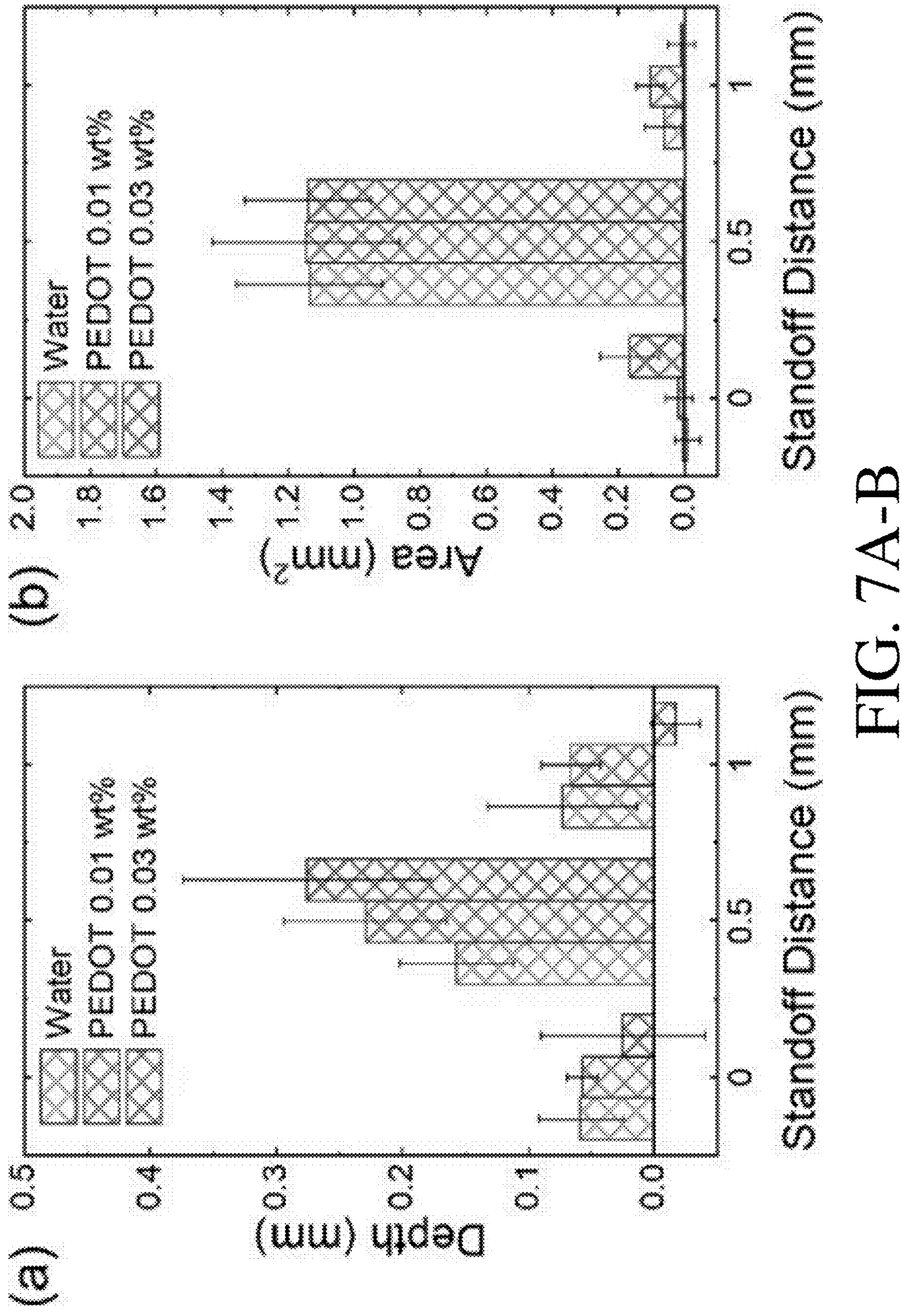

FIG. 7A-B: The crater's maximum depth (a) and profile area (b) due to bubble collapsed induced cavitation. Five independent stone damage experiments were conducted on BegoStones under each condition for both the small OD (0.25 mm) and large OD (3 mm) settings. As mentioned in the discussion section, the stone damage observed at the small OD (0.25 mm) setting was attributed to the thermal decomposition only. And the damage observed at the large OD (3 mm) setting was the combination of both thermal decomposition and cavitation. To determine the cavitation-induced crater's volume under a specific experimental condition, the average value of thermal decomposition-induced crater's volume was subtracted from the 5 independent results obtained in the large OD setting. The average value and standard deviation of these differences were plotted as the meshed bars in FIG. 3(*f*). The same calculation was applied to the maximum depth and profile area shown.

FIG. 8A-B: The temporal change of bubble width in three different fluids at (a) SD=0.5 mm and (b) SD=1 mm. There is no statistically significant difference in maximum bubble width at each SD.

Figure 9:
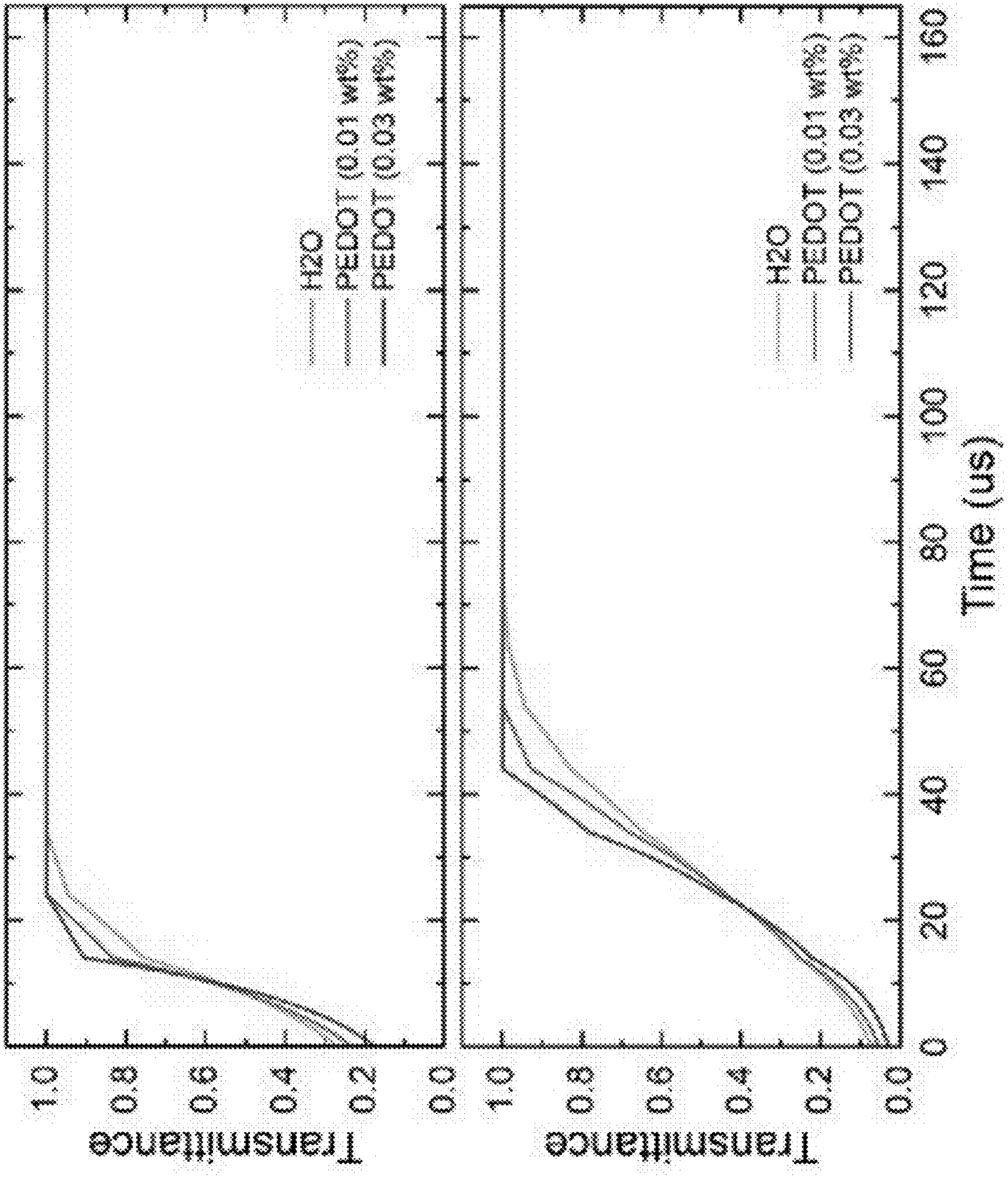

FIG. 9: Calculated time-dependent transmittance of 2120 nm light in different fluids at the SD=0.5 mm (top) and 1 mm (bottom).

Figure 10:
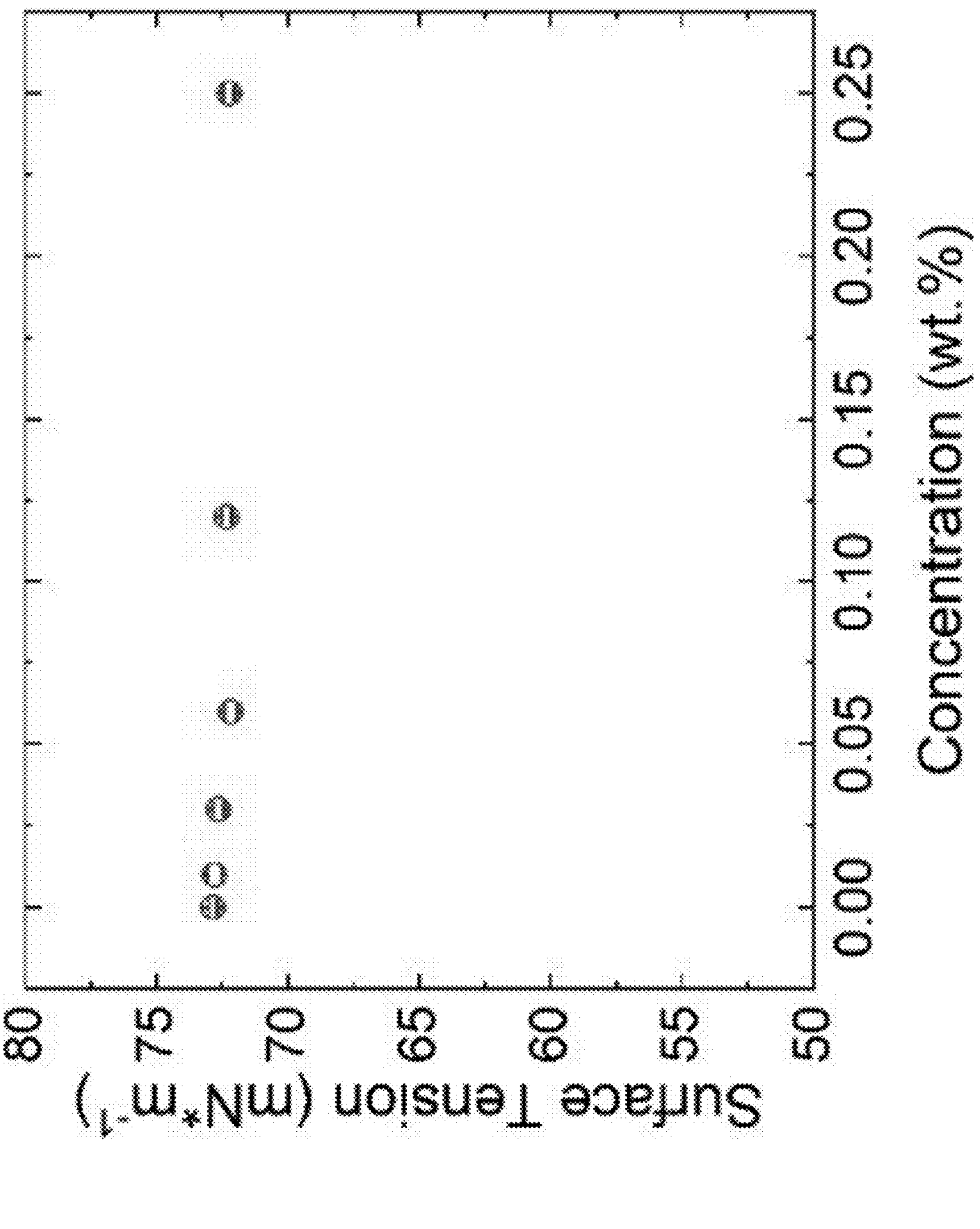

FIG. 10: Surface tension of $H_2O$ and PEDOT: PSS solutions with different concentrations. The surface tension was measured using the automatic surface tensiometer (BZY-201, Shanghai Fangrui Instrument Co., Ltd, Shanghai, China). Five independent measurements were made for each solution and the averaged values were plotted.

Figure 11:
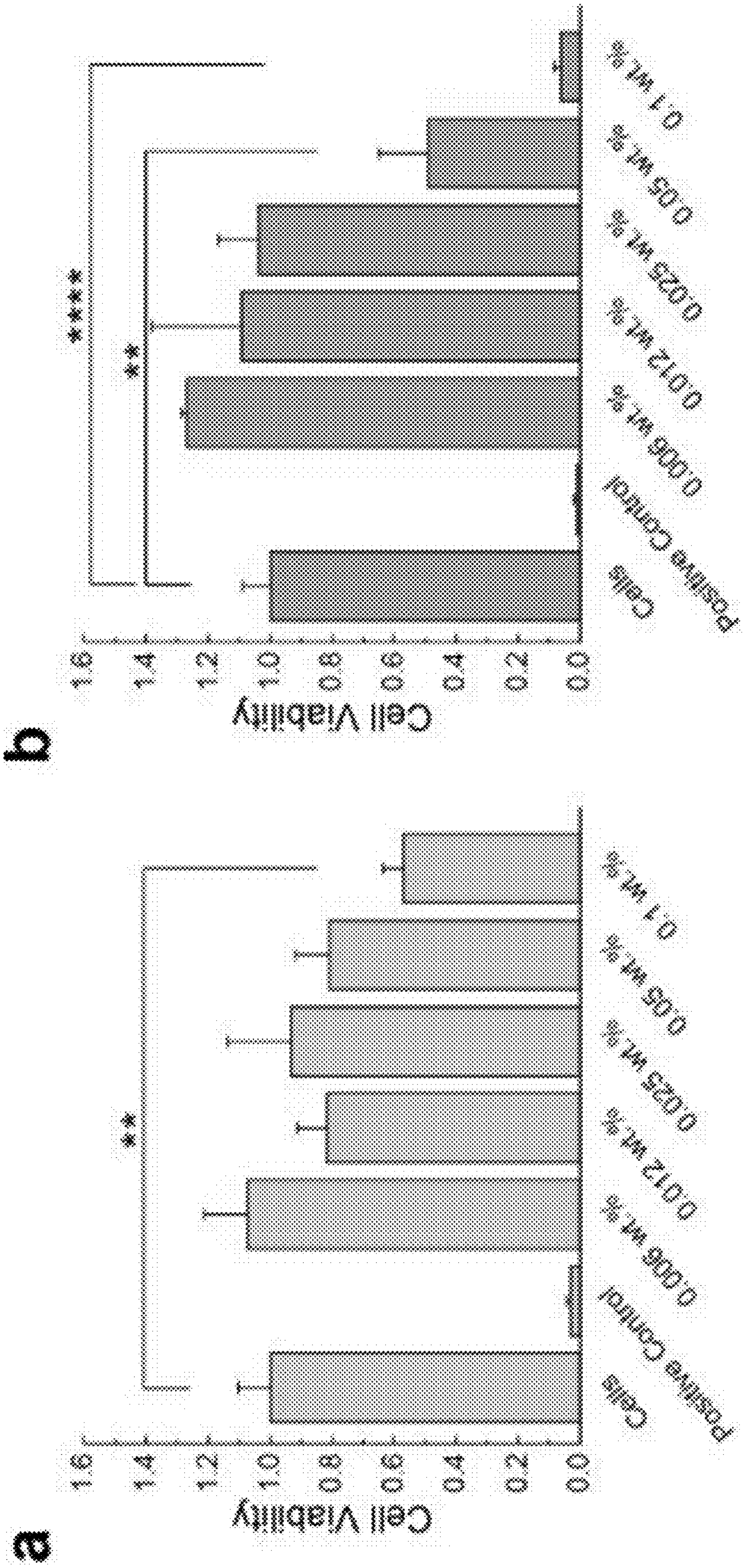

FIG. 11A-B: Viability of mIMCD-3 cells, measured with a MTT assay, after incubation with increasing concentrations of PEDOT: PSS. Exposure to triton X-100 (10% in PBS, 30 s) was used as a positive control to decrease cell viability. (a) 1 h incubation. (b) 24 h incubation. Significance was measured using 1-way ANOVA with Dunnett's multiple comparisons post hoc.  $p<0.01$, ** $p<0.0001$, ns—not significant comparison are not presented.

Figure 12:
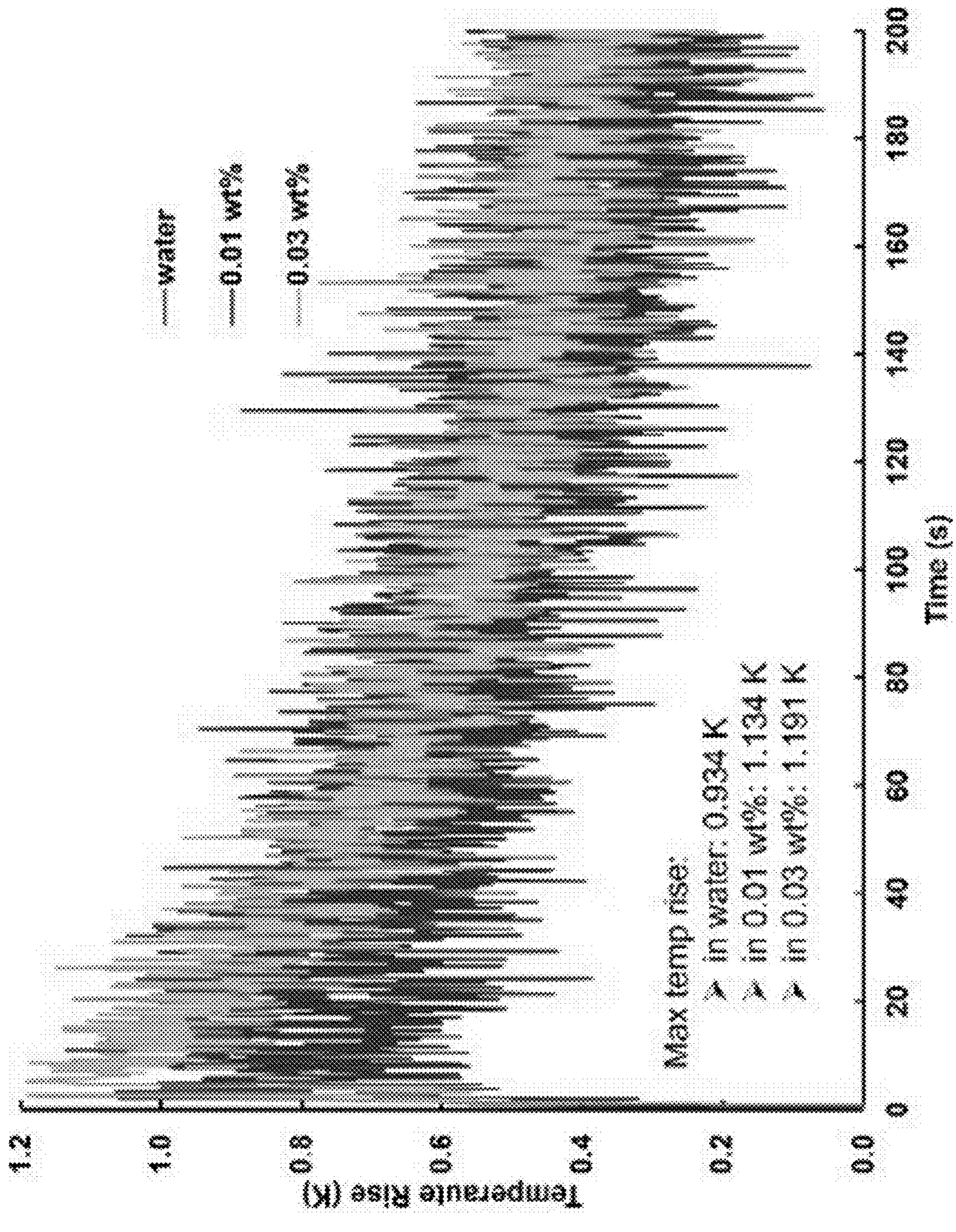

FIG. 12: Temporal temperature change of the fluids during the LL for 60 pulses (The laser was turned off at t=3 s).

FIG. 13A-D: (a) Scheme of ITO nanocrystal synthesis. (b-d) TEM image (b), size distribution (c), and X-ray diffraction pattern (d) of ITO nanocrystals.

Figure 14:
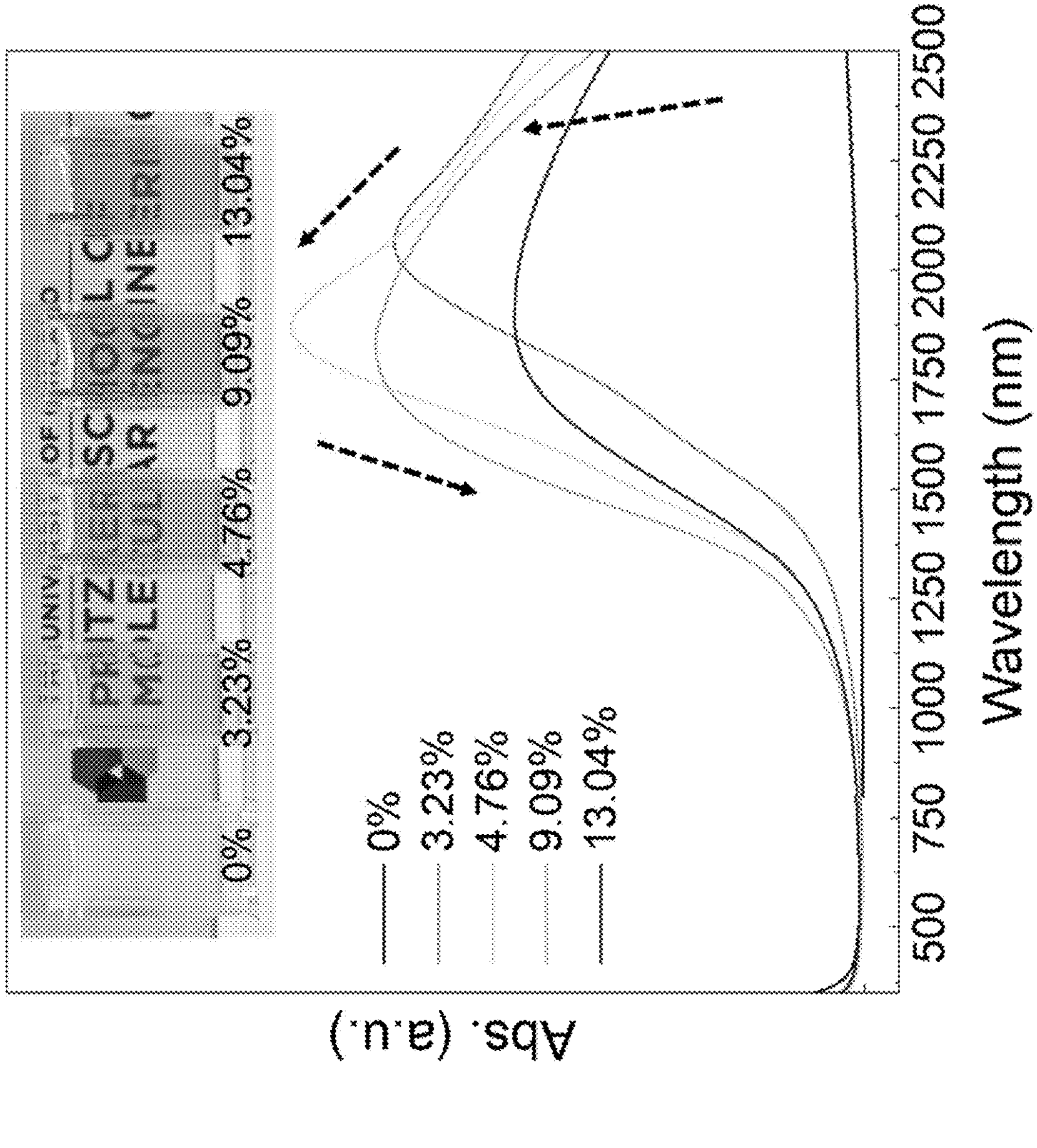

FIG. 14: Absorption spectra of ITO nanofluids at different feeding ratios (inset: photo of 1 wt. % ITO nanofluids with various feeding ratios). Water absorption peaks were subtracted to reveal ITO NPs' intrinsic absorption.

FIG. 15A-F: (a) Photos of ITO (left) and PEDOT: PSS (right) nanofluids. (b-c) Absorption spectra of ITO (b, 4.76% feeding ratio) and PEDOT: PSS (c) nanofluids. (d) Absorption coefficient vs. concentration of ITO (left) and PEDOT: PSS (right) nanofluids. (e) Average visible-spectrum transmittance of ITO and PEDOT: PSS nanofluids. (f) Comparison of absorption coefficient enhancement for 0.5 wt. % ITO vs. 0.03 wt. % PEDOT: PSS nanofluid.

FIG. 16A-F: (a) Appearance of nanofluids with BegoStone immersed for 5 min. (b) BegoStone view in ITO nanofluid under ureteroscope. (c) TEM image of $SiO_2$-coated ITO nanoparticles. (d-e) Zeta potential (d) and hydrodynamic diameter (e) of bare ITO, PAA-modified ITO (ITO-PAA), and $SiO_2$-coated ITO (ITO@$SiO_2$) nanofluids. (f) BegoStone view in ITO@$SiO_2$ nanofluid under ureteroscope.

FIG. 17A-B: (a) Photos of laser-produced craters on BegoStones. (b) Crater volume measurements from (a).

FIG. 18A-C: (a) Scheme of cytotoxicity test. (b-c) Viability of mouse kidney cells measured by MTT assay after 1 (b) and 24 hours (c) incubation with 0.25 wt. % ITO@$SiO_2$ nanofluid.

DETAILED DESCRIPTION

Holmium: yttrium-aluminum-garnet (Ho:YAG) laser lithotripsy effectively treats urinary stones, with increasing application for treating this prevalent condition in the U.S. The ablation efficiency of Ho:YAG laser lithotripsy can be enhanced through various approaches, including laser source setting adjustments and medium modification methods.

Nanoplasmonic engineering strategies improve ablation efficiency of laser lithotripsy by incorporating nanoparticles into the lithotripsy medium surrounding the stone. The nanoparticles, having diameters from about 1 nm to about 250 nm, enhance absorption efficiency of laser energy. For organic polymer nanoparticles such as poly(3,4-ethylenedioxythiophene) polystyrene sulfonate (PEDOT: PSS), diameters from about 50 nm to about 250 nm prove effective. The nanoparticles can be present in concentrations from about 0.001 wt. % to about 10 wt. %, with PEDOT: PSS specifically effective at concentrations from about 0.006 wt. % to about 0.03 wt. %.

Stone ablation efficiency increases by 38-727% when using dusting mode (0.2 J, 20 Hz) laser lithotripsy in 0.03 wt. % PEDOT: PSS nanofluid across fiber tip-to-stone standoff distances of 0-1 mm. The enhanced near-infrared (NIR) absorbance promotes vapor bubble formation between the laser fiber tip and target obstructions, increasing laser energy transmission to the stone surface and enhancing stone absorbance through fluid-filled pores. The process combines photothermal decomposition and cavitation damage mechanisms.

Multiple lithotripsy media with different nanoparticle diameters can be alternated during procedures to modify light absorption characteristics and efficiency. The wavelength of laser energy typically ranges from about 750 nm to about 2500 nm, with specific applications utilizing wavelengths from about 1800 nm to about 2200 nm.

The nanoparticles may comprise organic polymers such as PEDOT: PSS or inorganic compounds such as indium tin oxide. When using PEDOT: PSS nanoparticles, holmium lasers prove effective, while thulium lasers work effectively with indium tin oxide nanoparticles. Cytotoxicity testing of PEDOT: PSS nanofluid demonstrates favorable biocompatibility when concentration and application duration are controlled. This absorption coefficient modification approach remains compatible with laser setting modulation methods for enhanced laser lithotripsy outcomes.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

As noted herein, the disclosed embodiments have been presented for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, compositions, systems and apparatuses/devices that may further include any and all elements from any other disclosed methods, compositions, systems, and devices. In other words, elements from one or another disclosed embodiments may be interchangeable with elements from other disclosed embodiments. Moreover, some further embodiments may be realized by combining one and/or another feature disclosed herein with methods, compositions, systems and devices, and one or more features thereof, disclosed in materials incorporated by reference. In addition, one or more features/elements of disclosed embodiments may be removed and still result in patentable subject matter (and thus, resulting in yet more embodiments of the subject disclosure). Furthermore, some embodiments correspond to methods, compositions, systems, and devices which specifically lack one and/or another element, structure, and/or steps (as applicable), as compared to teachings of the prior art, and therefore represent patentable subject matter and are distinguishable therefrom (i.e. claims directed to such embodiments may contain negative limitations to note the lack of one or more features prior art teachings).

When describing the molecular detecting methods, systems and devices, terms such as linked, bound, connect, attach, interact, and so forth should be understood as referring to linkages that result in the joining of the elements being referred to, whether such joining is permanent or potentially reversible. These terms should not be read as requiring a specific bond type except as expressly stated.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, the term "functionally coupled" generally refers to the binding, joining, or combining of two or more molecules such that the resultant combination comprises at least one functional property. In some cases, the resultant combination of the two or more molecules maintains one or more functional properties of one or more of the uncoupled molecules. In other cases, the resultant combination yields a functional property not previously present in the individual, uncoupled molecules. In some cases, "functional coupling" includes the binding, joining, or combining of two or more molecules via chemical means (e.g., covalent or non-covalent interaction). As described further herein, in some cases, the "functional coupling" of two or more molecules results in the formation of a junction having certain electrical and/or biochemical properties.

"About" is used to provide flexibility to a numerical range endpoint by providing that a given value may be "slightly above" or "slightly below" the endpoint without affecting the desired result.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

As used herein, the terms "prevent," "preventing," "prevention," "prophylactic treatment" and the like refer to reducing the probability of developing a disease, disorder or condition in a subject, who does not have, but is at risk of or susceptible to developing a disease, disorder or condition.

The term "effective amount" or "therapeutically effective amount" refers to an amount sufficient to effect beneficial or desirable biological and/or clinical results.

As used herein, the term "administering" an agent, such as a therapeutic entity to an animal or cell, is intended to refer to dispensing, delivering, or applying the substance to the intended target. In terms of the therapeutic agent, the term "administering" is intended to refer to contacting or dispensing, delivering or applying the therapeutic agent to a subject by any suitable route for delivery of the therapeutic agent to the desired location in the animal, including delivery by either the parenteral or oral route, intramuscular injection, subcutaneous/intradermal injection, intravenous injection, intrathecal administration, buccal administration, transdermal delivery, topical administration, and administration by the intranasal or respiratory tract route.

The term "disease" as used herein includes, but is not limited to, any abnormal condition and/or disorder of a structure or a function that affects a part of an organism. It may be caused by an external factor, such as an infectious disease, injury, etc. or by internal dysfunctions, such as cancer, cancer metastasis, and the like. In some embodiments, the disease comprises kidney disease.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. The methods and compositions disclosed herein can be used on a sample either in vitro (for example, on isolated cells or tissues) or in vivo in a subject (i.e., living organism, such as a patient). In some embodiments, the subject comprises a human who is undergoing treatment using a system and/or method as prescribed herein.

Unless otherwise defined, all technical terms used herein have the same meaning as commonly understood by one of ordinary skill in the art to which this disclosure belongs.

2. DEVICES, SYSTEMS, AND METHODS

Nanofluid enhancement of kidney stone treatment can be achieved through incorporation of poly(3,4-ethylenedioxythiophene) polystyrene sulfonate (PEDOT: PSS) nanoparticles into the lithotripsy medium. The PEDOT: PSS nanoparticles, present at concentrations from about 0.006 wt. % to about 0.03 wt. %, enhance the ablation efficiency of holmium: YAG laser lithotripsy. At 0.03 wt. % concentration, PEDOT: PSS solution increases the Ho:YAG laser absorption coefficient by 25% compared to water.

The enhancement in stone ablation efficiency ranges from 38% to 727% across multiple standoff distances. This improvement stems from several mechanisms: rapid vapor tunnel establishment between the laser fiber tip and target obstructions, enhanced laser energy absorption due to nanofluid infiltration into stone pores, and increased cavitational damage from accelerated vapor bubble expansion and collapse, which aids in debris removal.

Cell viability assessments and temperature measurements demonstrate the biocompatibility of the nanofluid approach. The nanoparticles, having diameters from about 50 nm to about 250 nm, operate effectively with laser energy wavelengths from about 1800 nm to about 2200 nm when using holmium laser sources.

The near-infrared absorber-based efficiency improvements advance laser lithotripsy capabilities while maintaining safety parameters. This approach remains compatible with existing laser setting modulation methods and can be implemented alongside other treatment enhancement strategies, including the use of multiple lithotripsy media with varying nanoparticle diameters to modify light absorption characteristics and efficiency during procedures.

The present disclosure provides, in at least one aspect, methods of performing laser lithotripsy, the method comprising introducing a lithotripsy medium comprising nanoparticles into a body cavity of a subject, wherein the body cavity of the subject comprises one or more target obstructions, and applying laser energy through the lithotripsy medium to disrupt the one or more target obstructions, wherein the nanoparticles have a diameter configured to enhance absorption efficiency of the laser energy.

In some embodiments, the laser energy comprises a wavelength configured to enhance absorption efficiency of the laser energy by the lithotripsy medium.

In some embodiments, the wavelength of the laser energy is from about 750 nm to about 2500 nm. In some embodiments, the wavelength of the laser energy is from about 750 nm to about 2000 nm. In some embodiments, the wavelength of the laser energy is from about 750 nm to about 1500 nm. In some embodiments, the wavelength of the laser energy is from about 750 nm to about 1000 nm. In some embodiments, the wavelength of the laser energy is from about 1000 nm to about 2500 nm. In some embodiments, the wavelength of the laser energy is from about 1500 nm to about 2500 nm. In some embodiments, the wavelength of the laser energy is from about 2000 nm to about 2500 nm. In some embodiments, the wavelength of the laser energy is from about 1000 nm to about 2000 nm. In some embodiments, the wavelength of the laser energy is from about 1500 nm to about 2000 nm. In some embodiments, the wavelength of the laser energy is from about 1000 nm to about 1500 nm.

In some embodiments, the diameter of the nanoparticles is from about 1 nm to about 250 nm. In some embodiments, the diameter of the nanoparticles is from about 1 nm to about 200 nm. In some embodiments, the diameter of the nanoparticles is from about 1 nm to about 150 nm. In some embodiments, the diameter of the nanoparticles is from about 1 nm to about 100 nm. In some embodiments, the diameter of the nanoparticles is from about 1 nm to about 50 nm. In some embodiments, the diameter of the nanoparticles is from about 50 nm to about 250 nm. In some embodiments, the diameter of the nanoparticles is from about 100 nm to about 250 nm. In some embodiments, the diameter of the nanoparticles is from about 150 nm to about 250 nm. In some embodiments, the diameter of the nanoparticles is from about 200 nm to about 250 nm. In some embodiments, the diameter of the nanoparticles is from about 50 nm to about 200 nm. In some embodiments, the diameter of the nanoparticles is from about 100 nm to about 200 nm. In some embodiments, the diameter of the nanoparticles is from about 50 nm to about 150 nm.

In some embodiments, the nanoparticles are present in the lithotripsy medium at a concentration from about 0.001 wt. % to about 10 wt. %. In some embodiments, the nanoparticles are present in the lithotripsy medium at a concentration from about 0.001 wt. % to about 7.5 wt. %. In some embodiments, the nanoparticles are present in the lithotripsy medium at a concentration from about 0.001 wt. % to about 5 wt. %. In some embodiments, the nanoparticles are present in the lithotripsy medium at a concentration from about 0.001 wt. % to about 2.5 wt. %. In some embodiments, the nanoparticles are present in the lithotripsy medium at a concentration from about 0.001 wt. % to about 1 wt. %. In some embodiments, the nanoparticles are present in the lithotripsy medium at a concentration from about 2.5 wt. % to about 10 wt. %. In some embodiments, the nanoparticles are present in the lithotripsy medium at a concentration from about 5 wt. % to about 10 wt. %. In some embodiments, the nanoparticles are present in the lithotripsy medium at a concentration from about 7.5 wt. % to about 10 wt. %. In some embodiments, the nanoparticles are present in the lithotripsy medium at a concentration from about 2.5 wt. % to about 7.5 wt. %. In some embodiments, the nanoparticles are present in the lithotripsy medium at a concentration from about 1 wt. % to about 5 wt. %.

In some embodiments, the nanoparticles are comprised of at least one organic polymer.

In some embodiments, the at least one organic polymer comprises poly(3,4-ethylenedioxythiophene) polystyrene sulfonate (PEDOT: PSS).

In some embodiments, the wavelength of the laser energy is from about 1800 nm to about 2200 nm. In some embodiments, the wavelength of the laser energy is from about 1800 nm to about 2100 nm. In some embodiments, the wavelength of the laser energy is from about 1800 nm to about 2000 nm. In some embodiments, the wavelength of the laser energy is from about 1800 nm to about 1900 nm. In some embodiments, the wavelength of the laser energy is from about 1900 nm to about 2200 nm. In some embodiments, the wavelength of the laser energy is from about 2000 nm to about 2200 nm. In some embodiments, the wavelength of the laser energy is from about 2100 nm to about 2200 nm. In some embodiments, the wavelength of the laser energy is from about 1900 nm to about 2100 nm. In some embodiments, the wavelength of the laser energy is from about 2000 nm to about 2100 nm. In some embodiments, the wavelength of the laser energy is from about 1900 nm to about 2000 nm.

In some embodiments, the diameter of the nanoparticles is from about 50 nm to about 250 nm. In some embodiments, the diameter of the nanoparticles is from about 50 nm to about 200 nm. In some embodiments, the diameter of the nanoparticles is from about 50 nm to about 150 nm. In some embodiments, the diameter of the nanoparticles is from about 50 nm to about 100 nm. In some embodiments, the diameter of the nanoparticles is from about 100 nm to about 250 nm. In some embodiments, the diameter of the nanoparticles is from about 150 nm to about 250 nm. In some embodiments, the diameter of the nanoparticles is from about 200 nm to about 250 nm. In some embodiments, the diameter of the nanoparticles is from about 100 nm to about 200 nm. In some embodiments, the diameter of the nanoparticles is from about 150 nm to about 200 nm. In some embodiments, the diameter of the nanoparticles is from about 100 nm to about 150 nm.

In some embodiments, the nanoparticles are present in the lithotripsy medium at a concentration from about 0.006 wt. % to about 0.03 wt. %. In some embodiments, the nanoparticles are present in the lithotripsy medium at a concentration from about 0.006 wt. % to about 0.025 wt. %. In some embodiments, the nanoparticles are present in the lithotripsy medium at a concentration from about 0.006 wt. % to about 0.02 wt. %. In some embodiments, the nanoparticles are present in the lithotripsy medium at a concentration from about 0.006 wt. % to about 0.015 wt. %. In some embodiments, the nanoparticles are present in the lithotripsy medium at a concentration from about 0.006 wt. % to about 0.01 wt. %. In some embodiments, the nanoparticles are present in the lithotripsy medium at a concentration from about 0.01 wt. % to about 0.03 wt. %. In some embodiments, the nanoparticles are present in the lithotripsy medium at a concentration from about 0.015 wt. % to about 0.03 wt. %. In some embodiments, the nanoparticles are present in the lithotripsy medium at a concentration from about 0.02 wt. % to about 0.03 wt. %. In some embodiments, the nanoparticles are present in the lithotripsy medium at a concentration from about 0.025 wt. % to about 0.03 wt. %. In some embodiments, the nanoparticles are present in the lithotripsy medium at a concentration from about 0.01 wt. % to about 0.025 wt. %.

In some embodiments, the laser energy is applied using a holmium laser.

In some embodiments, the nanoparticles are comprised of at least one inorganic compound.

In some embodiments, the at least one inorganic compound comprises indium tin oxide.

In some embodiments, the wavelength of the laser energy is from about 1800 nm to about 2200 nm. In some embodiments, the wavelength of the laser energy is from about 1800 nm to about 2100 nm. In some embodiments, the wavelength of the laser energy is from about 1800 nm to about 2000 nm. In some embodiments, the wavelength of the laser energy is from about 1800 nm to about 1900 nm. In some embodiments, the wavelength of the laser energy is from about 1900 nm to about 2200 nm. In some embodiments, the wavelength of the laser energy is from about 2000 nm to about 2200 nm. In some embodiments, the wavelength of the laser energy is from about 2100 nm to about 2200 nm. In some embodiments, the wavelength of the laser energy is from about 1900 nm to about 2100 nm. In some embodiments, the wavelength of the laser energy is from about 2000 nm to about 2100 nm. In some embodiments, the wavelength of the laser energy is from about 1900 nm to about 2000 nm.

In some embodiments, the diameter of the nanoparticles is from about 1 nm to about 100 nm. In some embodiments, the diameter of the nanoparticles is from about 1 nm to about 75 nm. In some embodiments, the diameter of the nanoparticles is from about 1 nm to about 50 nm. In some embodiments, the diameter of the nanoparticles is from about 1 nm to about 25 nm. In some embodiments, the diameter of the nanoparticles is from about 25 nm to about 100 nm. In some embodiments, the diameter of the nanoparticles is from about 50 nm to about 100 nm. In some embodiments, the diameter of the nanoparticles is from about 75 nm to about 100 nm. In some embodiments, the diameter of the nanoparticles is from about 25 nm to about 75 nm. In some embodiments, the diameter of the nanoparticles is from about 50 nm to about 75 nm. In some embodiments, the diameter of the nanoparticles is from about 25 nm to about 50 nm.

In some embodiments, the nanoparticles are present in the lithotripsy medium at a concentration from about 0.1 wt. % to about 1 wt. %. In some embodiments, the nanoparticles are present in the lithotripsy medium at a concentration from about 0.1 wt. % to about 0.8 wt. %. In some embodiments, the nanoparticles are present in the lithotripsy medium at a concentration from about 0.1 wt. % to about 0.6 wt. %. In some embodiments, the nanoparticles are present in the lithotripsy medium at a concentration from about 0.1 wt. % to about 0.4 wt. %. In some embodiments, the nanoparticles are present in the lithotripsy medium at a concentration from about 0.1 wt. % to about 0.2 wt. %. In some embodiments, the nanoparticles are present in the lithotripsy medium at a concentration from about 0.2 wt. % to about 1 wt. %. In some embodiments, the nanoparticles are present in the lithotripsy medium at a concentration from about 0.4 wt. % to about 1 wt. %. In some embodiments, the nanoparticles are present in the lithotripsy medium at a concentration from about 0.6 wt. % to about 1 wt. %. In some embodiments, the nanoparticles are present in the lithotripsy medium at a concentration from about 0.8 wt. % to about 1 wt. %. In some embodiments, the nanoparticles are present in the lithotripsy medium at a concentration from about 0.2 wt. % to about 0.8 wt. %.

In some embodiments, the laser energy is applied using a thulium laser.

In some embodiments, applying the laser energy comprises generating vapor bubbles in the lithotripsy medium between a laser fiber tip and the one or more target obstructions.

In some embodiments, the one or more target obstructions comprise kidney stones.

In some embodiments, the method further comprises providing at least a second lithotripsy medium comprising nanoparticles having a different diameter than the nanoparticles in the first lithotripsy medium, and alternating between the first and second lithotripsy mediums during the laser lithotripsy procedure to modify light absorption characteristics and/or efficiency.

In some embodiments, the first lithotripsy medium provides enhanced absorption efficiency at a first wavelength and the second lithotripsy medium provides enhanced absorption efficiency at a second wavelength.

The present disclosure provides, in at least another aspect, systems for performing laser lithotripsy, comprising a laser source configured to generate laser energy, a fluid delivery component configured to deliver a lithotripsy medium comprising nanoparticles having a diameter selected to enhance absorption efficiency at the wavelength of the laser energy, and an optical fiber configured to deliver the laser energy to one or more target obstructions through the lithotripsy medium.

In some embodiments, the laser energy comprises a wavelength configured to enhance absorption efficiency of the laser energy by the lithotripsy medium.

In some embodiments, the wavelength of the laser energy is from about 750 nm to about 2500 nm. In some embodiments, the wavelength of the laser energy is from about 750 nm to about 2000 nm. In some embodiments, the wavelength of the laser energy is from about 750 nm to about 1500 nm. In some embodiments, the wavelength of the laser energy is from about 750 nm to about 1000 nm. In some embodiments, the wavelength of the laser energy is from about 1000 nm to about 2500 nm. In some embodiments, the wavelength of the laser energy is from about 1500 nm to about 2500 nm. In some embodiments, the wavelength of the laser energy is from about 2000 nm to about 2500 nm. In some embodiments, the wavelength of the laser energy is from about 1000 nm to about 2000 nm. In some embodiments, the wavelength of the laser energy is from about 1500 nm to about 2000 nm. In some embodiments, the wavelength of the laser energy is from about 1000 nm to about 1500 nm.

In some embodiments, the diameter of the nanoparticles is from about 1 nm to about 250 nm. In some embodiments, the diameter of the nanoparticles is from about 1 nm to about 200 nm. In some embodiments, the diameter of the nanoparticles is from about 1 nm to about 150 nm. In some embodiments, the diameter of the nanoparticles is from about 1 nm to about 100 nm. In some embodiments, the diameter of the nanoparticles is from about 1 nm to about 50 nm. In some embodiments, the diameter of the nanoparticles is from about 50 nm to about 250 nm. In some embodiments, the diameter of the nanoparticles is from about 100 nm to about 250 nm. In some embodiments, the diameter of the nanoparticles is from about 150 nm to about 250 nm. In some embodiments, the diameter of the nanoparticles is from about 200 nm to about 250 nm. In some embodiments, the diameter of the nanoparticles is from about 50 nm to about 200 nm. In some embodiments, the diameter of the nanoparticles is from about 100 nm to about 200 nm. In some embodiments, the diameter of the nanoparticles is from about 50 nm to about 150 nm.

In some embodiments, the nanoparticles are present in the lithotripsy medium at a concentration from about 0.001 wt. % to about 10 wt. %. In some embodiments, the nanoparticles are present in the lithotripsy medium at a concentration from about 0.001 wt. % to about 7.5 wt. %. In some embodiments, the nanoparticles are present in the lithotripsy medium at a concentration from about 0.001 wt. % to about 5 wt. %. In some embodiments, the nanoparticles are present in the lithotripsy medium at a concentration from about 0.001 wt. % to about 2.5 wt. %. In some embodiments, the nanoparticles are present in the lithotripsy medium at a concentration from about 0.001 wt. % to about 1 wt. %. In some embodiments, the nanoparticles are present in the lithotripsy medium at a concentration from about 2.5 wt. % to about 10 wt. %. In some embodiments, the nanoparticles are present in the lithotripsy medium at a concentration from about 5 wt. % to about 10 wt. %. In some embodiments, the nanoparticles are present in the lithotripsy medium at a concentration from about 7.5 wt. % to about 10 wt. %. In some embodiments, the nanoparticles are present in the lithotripsy medium at a concentration from about 2.5 wt. % to about 7.5 wt. %. In some embodiments, the nanoparticles are present in the lithotripsy medium at a concentration from about 1 wt. % to about 5 wt. %.

In some embodiments, the nanoparticles are comprised of at least one organic polymer.

In some embodiments, the at least one organic polymer comprises poly(3,4-ethylenedioxythiophene) polystyrene sulfonate (PEDOT: PSS).

In some embodiments, the wavelength of the laser energy is from about 1800 nm to about 2200 nm. In some embodiments, the wavelength of the laser energy is from about 1800 nm to about 2100 nm. In some embodiments, the wavelength of the laser energy is from about 1800 nm to about 2000 nm. In some embodiments, the wavelength of the laser energy is from about 1800 nm to about 1900 nm. In some embodiments, the wavelength of the laser energy is from about 1900 nm to about 2200 nm. In some embodiments, the wavelength of the laser energy is from about 2000 nm to about 2200 nm. In some embodiments, the wavelength of the laser energy is from about 2100 nm to about 2200 nm. In some embodiments, the wavelength of the laser energy is from about 1900 nm to about 2100 nm. In some embodiments, the wavelength of the laser energy is from about 2000 nm to about 2100 nm. In some embodiments, the wavelength of the laser energy is from about 1900 nm to about 2000 nm.

In some embodiments, the diameter of the nanoparticles is from about 50 nm to about 250 nm. In some embodiments, the diameter of the nanoparticles is from about 50 nm to about 200 nm. In some embodiments, the diameter of the nanoparticles is from about 50 nm to about 150 nm. In some embodiments, the diameter of the nanoparticles is from about 50 nm to about 100 nm. In some embodiments, the diameter of the nanoparticles is from about 100 nm to about 250 nm. In some embodiments, the diameter of the nanoparticles is from about 150 nm to about 250 nm. In some embodiments, the diameter of the nanoparticles is from about 200 nm to about 250 nm. In some embodiments, the diameter of the nanoparticles is from about 100 nm to about 200 nm. In some embodiments, the diameter of the nanoparticles is from about 150 nm to about 200 nm. In some embodiments, the diameter of the nanoparticles is from about 100 nm to about 150 nm.

In some embodiments, the nanoparticles are present in the lithotripsy medium at a concentration from about 0.006 wt. % to about 0.03 wt. %. In some embodiments, the nanoparticles are present in the lithotripsy medium at a concentration from about 0.006 wt. % to about 0.025 wt. %. In some embodiments, the nanoparticles are present in the lithotripsy medium at a concentration from about 0.006 wt. % to about 0.02 wt. %. In some embodiments, the nanoparticles are present in the lithotripsy medium at a concentration from about 0.006 wt. % to about 0.015 wt. %. In some embodiments, the nanoparticles are present in the lithotripsy medium at a concentration from about 0.006 wt. % to about 0.01 wt. %. In some embodiments, the nanoparticles are present in the lithotripsy medium at a concentration from about 0.01 wt. % to about 0.03 wt. %. In some embodiments, the nanoparticles are present in the lithotripsy medium at a concentration from about 0.015 wt. % to about 0.03 wt. %. In some embodiments, the nanoparticles are present in the lithotripsy medium at a concentration from about 0.02 wt. % to about 0.03 wt. %. In some embodiments, the nanoparticles are present in the lithotripsy medium at a concentration from about 0.025 wt. % to about 0.03 wt. %. In some embodiments, the nanoparticles are present in the lithotripsy medium at a concentration from about 0.01 wt. % to about 0.025 wt. %.

In some embodiments, the laser source is a holmium laser.

In some embodiments, the nanoparticles are comprised of at least one inorganic compound.

In some embodiments, the at least one inorganic compound comprises indium tin oxide.

In some embodiments, the wavelength of the laser energy is from about 1800 nm to about 2200 nm. In some embodiments, the wavelength of the laser energy is from about 1800 nm to about 2100 nm. In some embodiments, the wavelength of the laser energy is from about 1800 nm to about 2000 nm. In some embodiments, the wavelength of the laser energy is from about 1800 nm to about 1900 nm. In some embodiments, the wavelength of the laser energy is from about 1900 nm to about 2200 nm. In some embodiments, the wavelength of the laser energy is from about 2000 nm to about 2200 nm. In some embodiments, the wavelength of the laser energy is from about 2100 nm to about 2200 nm. In some embodiments, the wavelength of the laser energy is from about 1900 nm to about 2100 nm. In some embodiments, the wavelength of the laser energy is from about 2000 nm to about 2100 nm. In some embodiments, the wavelength of the laser energy is from about 1900 nm to about 2000 nm.

In some embodiments, the diameter of the nanoparticles is from about 1 nm to about 100 nm. In some embodiments, the diameter of the nanoparticles is from about 1 nm to about 75 nm. In some embodiments, the diameter of the nanoparticles is from about 1 nm to about 50 nm. In some embodiments, the diameter of the nanoparticles is from about 1 nm to about 25 nm. In some embodiments, the diameter of the nanoparticles is from about 25 nm to about 100 nm. In some embodiments, the diameter of the nanoparticles is from about 50 nm to about 100 nm. In some embodiments, the diameter of the nanoparticles is from about 75 nm to about 100 nm. In some embodiments, the diameter of the nanoparticles is from about 25 nm to about 75 nm. In some embodiments, the diameter of the nanoparticles is from about 50 nm to about 75 nm. In some embodiments, the diameter of the nanoparticles is from about 25 nm to about 50 nm.

In some embodiments, the nanoparticles are present in the lithotripsy medium at a concentration from about 0.1 wt. % to about 1 wt. %. In some embodiments, the nanoparticles are present in the lithotripsy medium at a concentration from about 0.1 wt. % to about 0.8 wt. %. In some embodiments, the nanoparticles are present in the lithotripsy medium at a concentration from about 0.1 wt. % to about 0.6 wt. %. In some embodiments, the nanoparticles are present in the lithotripsy medium at a concentration from about 0.1 wt. % to about 0.4 wt. %. In some embodiments, the nanoparticles are present in the lithotripsy medium at a concentration from about 0.1 wt. % to about 0.2 wt. %. In some embodiments, the nanoparticles are present in the lithotripsy medium at a concentration from about 0.2 wt. % to about 1 wt. %. In some embodiments, the nanoparticles are present in the lithotripsy medium at a concentration from about 0.4 wt. % to about 1 wt. %. In some embodiments, the nanoparticles are present in the lithotripsy medium at a concentration from about 0.6 wt. % to about 1 wt. %. In some embodiments, the nanoparticles are present in the lithotripsy medium at a concentration from about 0.8 wt. % to about 1 wt. %. In some embodiments, the nanoparticles are present in the lithotripsy medium at a concentration from about 0.2 wt. % to about 0.8 wt. %.

In some embodiments, the laser source is a thulium laser.

In some embodiments, the fluid delivery component is configured to deliver a second lithotripsy medium comprising nanoparticles having a second diameter selected to modify light absorption characteristics and/or efficiency.

The present disclosure provides, in at least yet another aspect, methods of manufacturing a lithotripsy medium, comprising selecting a target wavelength for enhanced absorption of laser energy, synthesizing nanoparticles having a diameter selected to provide an absorption peak at the target wavelength, and dispersing the nanoparticles in the lithotripsy medium at a selected concentration.

3. MATERIALS AND METHODS

Aqueous dispersion of PEDOT: PSS conductive polymer (Clevios PH 1000) was purchased from MSE Supplies and used without further purification. The solution has a concentration of 1.2 wt. % and the average particle size is 30 nm. The solution was diluted by DI water into various concentrations.

Near-IR absorption spectroscopy: The NIR absorbance spectra of solutions were measured using a UV-Vis-NIR spectrophotometer (Cary 5000, Agilent, Santa Clara, CA, USA). During the measurement, the solution was filled in a cuvette with a path length of 0.2 mm (IR quartz, FireflySci, Inc. Northport, NY, USA) and the scan range was set to be 1350-2500 nm (resolution: 1 nm and scan rate: 600 nm/min). The slit width was 1 nm. An empty cuvette was used as the background when collecting data.

Visible transmission spectroscopy: The visible spectra were measured on the UV-Vis-NIR spectrophotometer (Cary 5000, Agilent, Santa Clara, CA, USA). The scan range was set to be 380-750 nm (resolution: 1 nm and scan rate: 600 nm/min). The slit width was 1 nm. A glass cuvette with a path length of 5 mm filled with water was used as the background when collecting data. The average transmittance of a solution in visible is calculated by:

$$\% \ T_{average} \frac{\int_{380}^{750} \% \ T_{measured} d\lambda}{\int_{380}^{750} d\lambda}$$

NIR diffusive reflectance: The NIR diffusive reflectance of the BegoStone samples was measured using a UV-Vis-NIR spectrometer (Shimadzu UV3600 Plus) equipped with an integrating sphere. The scan range was set to be 1950-2250 nm (resolution: 1 nm and scan rate: medium). The slit width was 1 nm. A standard white plate coated with BaSO4 was used as the reference. 30 μL of the fluid is dropped on the top surface of the BegoStone and it quickly diffused into the stone within 30 s and no liquid can be observed on the stone surface. For each fluid, same measurement was repeat on seven different stones to account for the variation in stones. The average of seven measurements and standard deviation (colored shade) were plotted in FIG. 2(*g*). Since BegoStone is very thick (6 mm), we assume no light can transmit through, so stone absorption=1−reflectance.

Figure 3:
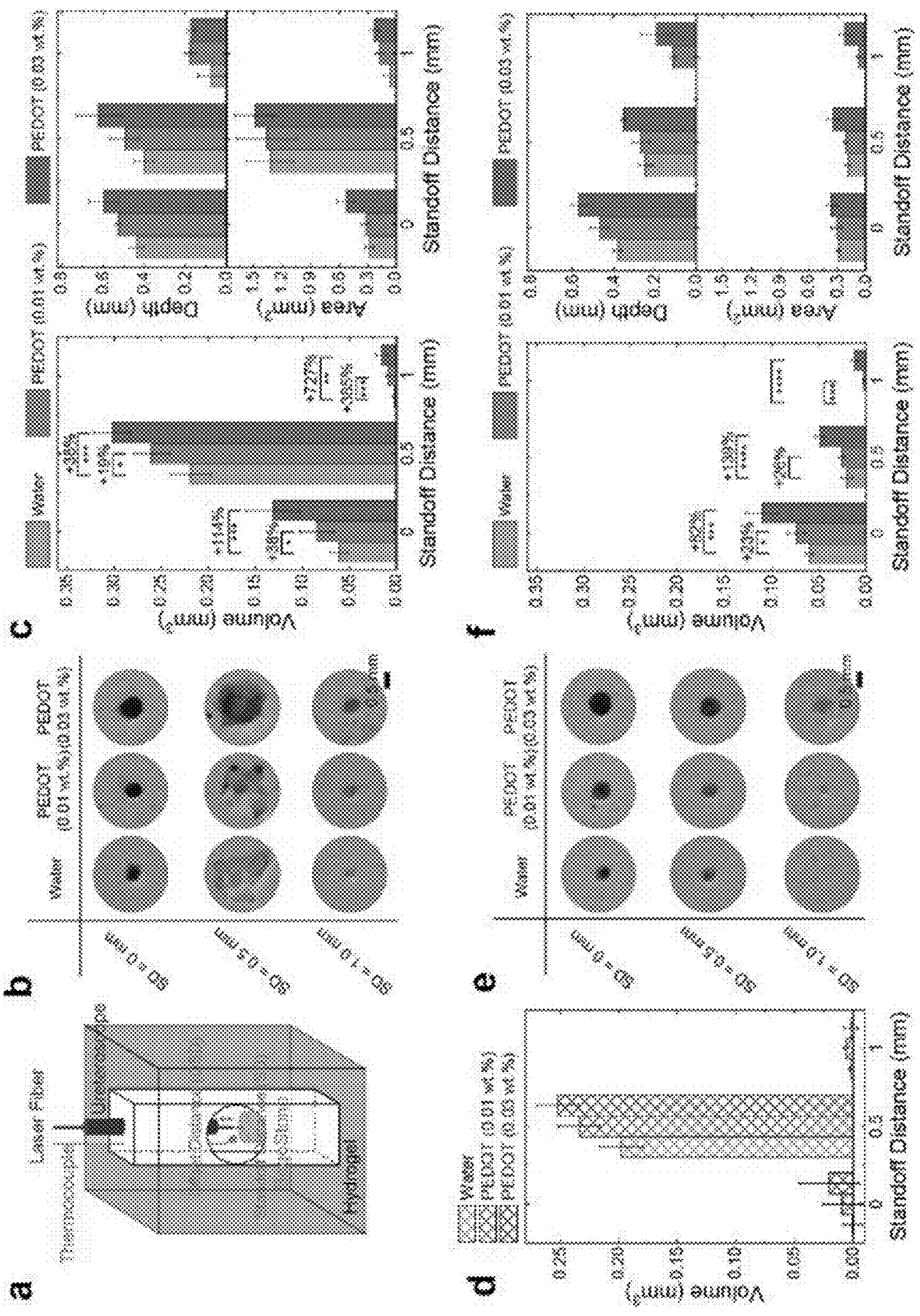
FIG. 3A-F: Stone damage assessment. (a) Schematic illustration of experimental setup. (b) Photos of damage craters on BegoStone samples produced in different PEDOT.

Stone Damage Assessment: To evaluate the impact of PEDOT: PSS nanofluids on the stone damage efficiency of LL, we treated artificial BegoStone phantoms (6×6 mm pre-soaked cylinders; 5:2 powder to water ratio, BEGO USA, Lincoln, RI, USA) in a cuvette by using a clinical Ho:YAG laser lithotripter (H Solvo 35-watt laser, Dornier MedTech, Munich, Germany). Within the cuvette, a thick layer of transparent hydrogel (Gelatin #1; Humimic Medical, SC, USA) was applied to its inner walls to simulate the soft boundary of kidney tissue, leaving a 12×12×40 mm3 cuboid space in the middle as depicted in FIG. 3(*a*). To further mimic a calyx environment of the kidney, a 3D-printed part with a spherical chamber of 5 mm in radius was fixed in the cuboid. The chamber was filled with 2 mL of PEDOT: PSS solutions at different concentrations (0 wt. %, 0.01 wt. %, and 0.03 wt. %) and the stone sample was positioned in its center. Additionally, a thermocouple was placed near the tissue boundary to record fluid temperature changes during LL. During the treatment, a flexible ureteroscope (Dornier AXISTM, with a 3.6 F working channel from Munich, Germany) with a 270 μm laser delivery fiber (Dornier SingleFlex 200, Munich, Germany) inserted through its working channel was placed perpendicularly to the stone surface. Laser pulses (60 pulses, n=5) were delivered at an energy level of Ep=0.2 J and a frequency of F=20 Hz in dusting mode at various fiber tip-to-stone standoff distances (SDs; 0, 0.5, and 1.0 mm). The resultant damage craters were then scanned by optical coherence tomography (OCT) to extract crater volumes, depths and profile areas.

Cell Culture: A murine epithelial cell line (mIMCD-3, ATCC, Manassas, VA, USA) was used for all experiments. Cells were cultured in Dulbecco's Modified Eagle Medium/Hams F-12 (DMEM/F-12; pH 7.4, #11320033, Thermo Fisher, Waltham, MA, USA), supplemented with 10% fetal bovine serum (FBS, #10437028, Thermo Fisher, Waltham, MA, USA). Cells were grown at 5% $CO_2$ at 37° C. and passaged upon reaching 80% confluency with a maximum passage number of 20.

MTT Assay: MIMCD-3 cells were seeded onto sterile 24-well plates (#3524, Corning Inc, Corning NY, USA) at a density of 150,000 cells per well. The cells were cultured overnight and incubated with PEDOT: PSS (0.006 wt. %-0.1 wt. %) for 1 h or 24 h. Control cells were incubated in DMEM/F-12 media for the duration of the treatment. Incubation with Triton X-100 (10% in Dulbecco's Phosphate Buffered Saline (PBS), 30 s exposure; X100-100ML, Millipore Sigma, Burlington, MA, USA) was used to damage cells, serving as a positive control. Cells were washed 3 times in PBS (#28374, Thermo Fisher, Waltham, MA, USA). Cells were incubated in DMEM (300.il; #31053028, Thermo Fisher) and 3-(4,5-dimethylthiazol-2-yl)-2,5-diphenyl tetrazolium bromide (MTT, 0.5 mg/ml, #V13154, Thermo Fisher, Waltham, MA, USA) for 1 h. Media was aspirated, and cells were incubated in dimethyl sulfoxide (300.il; DMSO, #D8418, Millipore Sigma) for 10 minutes in the dark. DMSO was transferred into a clear 96-well plate (#82050, VWR, Radnor, PA, USA) and absorbance was measured at 580 nm using a plate reader (SpectraMax iD3, Molecular Devices, San Jose, CA, USA).

4. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1: Optical Properties of PEDOT: PSS Nanofluid

Figure 4:
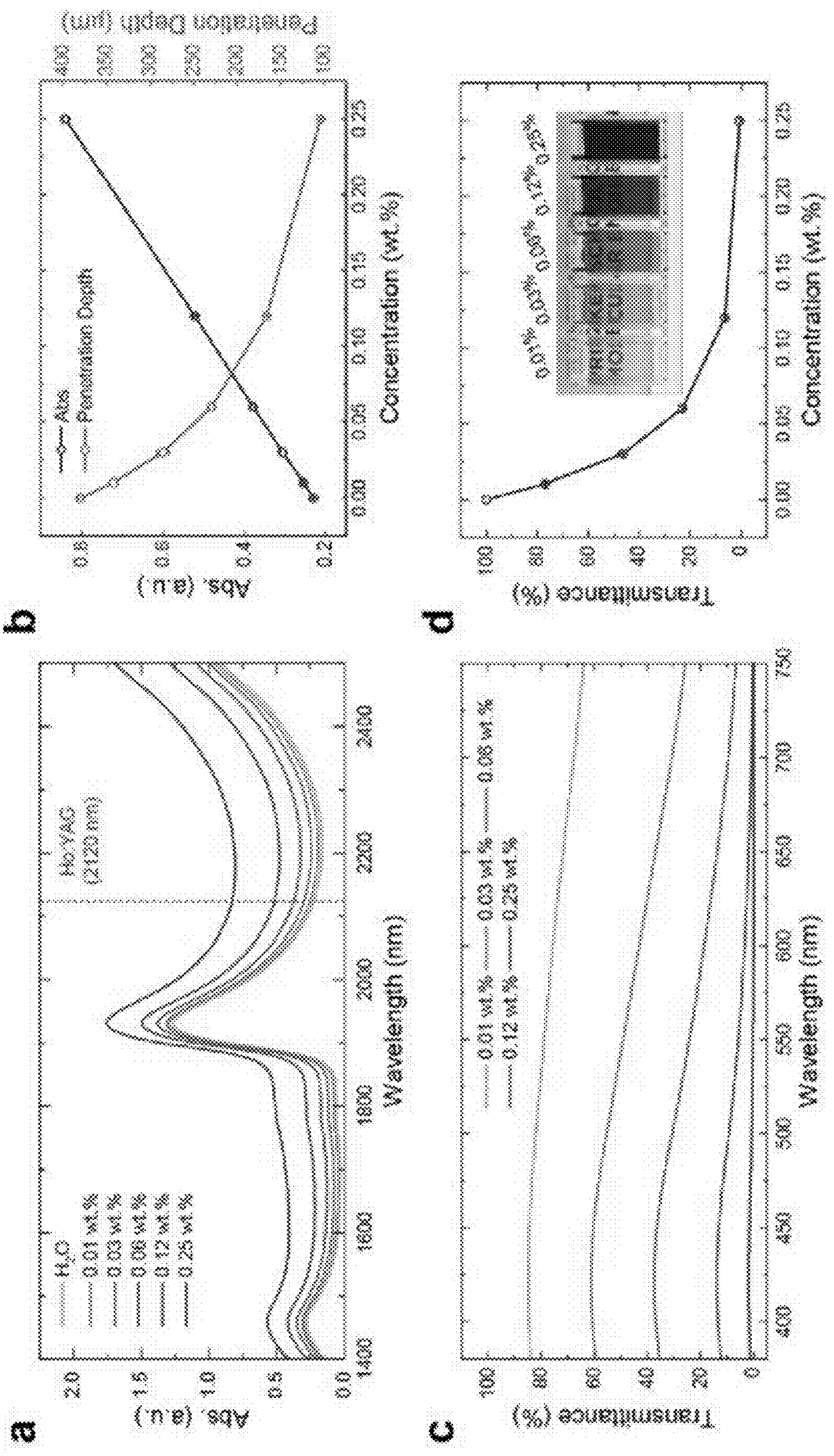

At the Ho:YAG wavelength of 2120 nm, PEDOT: PSS stands out as the most promising conductive polymer-based nanofluid because of its free-carrier absorption enabled by the PEDOT delocalized hole carriers and its water dispersibility achieved by the sulphonic groups in the PSS moiety. PEDOT: PSS finds widespread applications in flexible electronics, solar cells, IR sensors, and more. Its appeal lies in its tunable electrical conductivity, relative transparency to visible light, excellent thermal stability, and biocompatibility. Moreover, PEDOT: PSS nanoparticles (NPs) can be synthesized through colloidal routes, facilitating large-scale production at a relatively low cost. As depicted in FIG. 4(*a*), the addition of PEDOT: PSS NPs to water leads to a gradual increase in fluid absorbance within the NIR range. Of particular interest is the absorbance of fluids at 2120 nm, the operational wavelength of the Ho:YAG laser. Through plotting the absorbance at 2120 nm against the concentrations of PEDOT: PSS nanofluid, a linear correlation emerges between these parameters, showing the typical Beer's law behavior (FIG. 4(*b*)). As the concentration of the PEDOT: PSS nanofluid rises, the penetration depth of light at 2120 nm diminishes from 379.6±2.2 μm for pure water to 342.2±4.0 μm for 0.01 wt. % and further to 285.3±6.9 μm for the 0.03 wt. % PEDOT: PSS nanofluid. These decreases of penetration depth correspond to a 10% and 25% increase of absorbed power density.

While adding more PEDOT: PSS NPs in water can enhance the NIR absorption, it has an upper limit posed by the reduced visible clarity, a crucial factor for urologists to locate the stone and laser spot. The π-π* transition of PEDOT: PSS results in the absorption of visible light that makes the solution appear dark blue, especially at high concentrations (FIG. 4(*d*), inset). This strong visible absorption contradicts with the requirement of a clear field of view for the surgeon during the laser lithotripsy (LL). To determine the optimal concentration of PEDOT: PSS nanofluid for LL by considering both NIR absorbance enhancement and visibility, the transmittance of the solutions within the visible regime can be measured (FIG. 4(*c*)). The path length can be chosen to be 5 mm to approximate the typical searching and working distance between the ureteroscope and the kidney stone in clinical practice. The average visible transmittance of the nanofluids decreases with increasing PEDOT: PSS concentration, as expected. Upon inspecting the field of view under the ureteroscope, the kidney stone remains clearly visible with the concentration lower than 0.03 wt. % (FIG. 5).

Example 2: Stone Damage Assessment

The stone damage efficiency of LL can be assessed in a cuvette containing an artificial BegoStone phantom (6×6 mm cylinders) immersed in nanofluids with different concentrations (0, 0.1, and 0.3 wt. %). The cuvette's geometry is depicted in FIG. 3(*a*), and a ureteroscope-integrated laser fiber with an offset distance (OSD) of 3 mm can be placed atop the stone at various standoff distances (SDs) (0, 0.5, and 1.0 mm). In clinical practice, laser pulse energy and pulse frequency can be controlled to achieve different stone damage modes, such as "dusting", "fragmenting", and "pop-dusting". Operating in the dusting mode with a low pulse energy of 0.2 J and a high pulse frequency of 20 Hz pulverizes the stone into very fine particles. While maximizing photothermal ablation entails direct contact between the laser fiber tip and the stone surface (i.e., SD=0 mm), maintaining such contact presents challenges in clinical practices due to retropulsion.

FIG. 3(*b*) depicts the craters produced by delivering 60 laser pulses at SD=0, 0.5, and 1 mm in different PEDOT: PSS nanofluids, with the corresponding dimensional measurements summarized in FIG. 3(*c*). As the concentrations of PEDOT increase, the size of damage craters expands across all SDs. Blue tints can be consistently observed inside the craters when PEDOT: PSS nanofluids are employed. Such coloration may be attributed to the adherence of PEDOT: PSS NPs to the stone surface due to the local high temperatures induced by laser-stone interactions. Furthermore, compared to the regular and round craters produced at SD=0 and 1 mm, the profiles of the craters produced at SD=0.5 mm are larger and more irregular in all three fluids.

At each SD, a significant increase in crater volume occurs with the addition of PEDOT: PSS. For instance, at SD=0 mm, where photothermal ablation dominates, the stone treatment in 0.01 wt. % and 0.03 wt. % PEDOT: PSS nanofluids results in crater volume increases of 38% (0.0848±0.0182 mm3) and 114% (0.1313±0.0287 mm3), respectively, when compared to those produced in pure water (0.0614±0.0092 mm3) under the same conditions. This enhancement in ablation efficiency can be ascribed to the increase of both maximum crater depth and profile area (FIG. 3(*c*)). Similarly, as SD increases to 1 mm, although the ablation efficiency drops due to the attenuation of laser energy by the fluid, 0.03 wt. % PEDOT: PSS nanofluid exhibits a 727% enhancement in crater volume compared to water (0.01554±0.00652 mm3 vs. 0.00188±0.00173 mm3), demonstrating the advantages of using PEDOT: PSS nanofluids in extending the effective fiber-to-stone working distance during LL. For all three fluids tested, the greatest stone damage is produced at SD=0.5 mm with an enhancement of 19% in 0.01 wt. % and 38% in 0.03 wt %.

Example 3: Mechanisms of Nanofluid-Enhanced Ablation Efficiency

In clinical practice, LL is conducted on stones surrounded by saline, whose primary component is water with a relatively high absorption coefficient for 2120 nm Ho:YAG laser. When the pulsed laser is activated, the fluid around the fiber tip absorbs the photon energy, which converts to heat. Once the heat exceeds vaporization enthalpy (latent heat), vapor bubbles form and expand. The formation of vapor bubbles is critical for the destruction of urinary stones for two reasons: (1) the bubble collapse near the stone surface can induce mechanical damage to the stone other than conventional photothermal ablation theory for laser-material interactions, and (2) once the vapor bubble bridges the gap between the laser fiber tip and stone surface, i.e., SD>0 mm, the photon energy can be transmitted to the stone with minimal loss since water vapor has a much lower absorption coefficient compared to its liquid state, known as the Moses effect.

Contributions of Cavitation vs. Thermal Ablation

The mechanisms behind the enhanced ablation efficiency of LL can be investigated by differentiating the contributions of photothermal ablation and cavitation in different nanofluids. Stone damage experiments can be conducted where all parameters remain constant except for reducing the OSD between the laser fiber tip and the ureteroscope end from 3 mm to 0.25 mm. At such a short OSD, the ureteroscope tip can attract the cavitation bubble collapse away from the stone surface (FIG. 6), thus eliminating the contributions of bubble collapse to stone damage, especially when LL is performed in the non-direct-contact mode. The optical photos and dimensional measurements of the resultant craters are summarized in FIGS. 3(*e*) and 3(*f*), respectively. Compared to the stone damage produced at large OSD of 3 mm (FIG. 3(*b*)), the damage craters produced at OSD=0.25 mm become circular at all SDs, and blue tints can be observed in those produced from nanofluids. Quantitatively, at SD=0 mm, since the bubble collapse induced stone damage cannot be isolated using a short OSD, there are no statistically significant differences between the crater volumes produced at the two different OSDs in water. In contrast, at SD=0.5 mm and 1 mm, the crater volumes are significantly reduced by 90% and 100% in water, after mitigating bubble collapse, suggesting the critical role of cavitation in stone dusting. The volume differences between two OSD cases plotted in FIG. 3(*d*) show that the contributions of cavitation can increase with the PEDOT: PSS concentrations, especially at SD=0.5 mm. Compared to those in water, the increased volumes of the craters in PEDOT: PSS nanofluids suggest an enhanced cavitation damage, indicating that the additional of PEDOT: PSS NPs into the fluid affects the behavior of the cavitation bubble. Additionally, at OSD=0.25 mm, the volume, depth, and profile area of the craters all decrease with SD but increase with the concentration of nanofluids (FIG. 7), suggesting that the PEDOT: PSS nanoparticles enhance the photothermal ablation effects via increasing the NIR absorbance during the laser-stone interaction.

Bubble Dynamics and Energy Transmission

Figure 1:
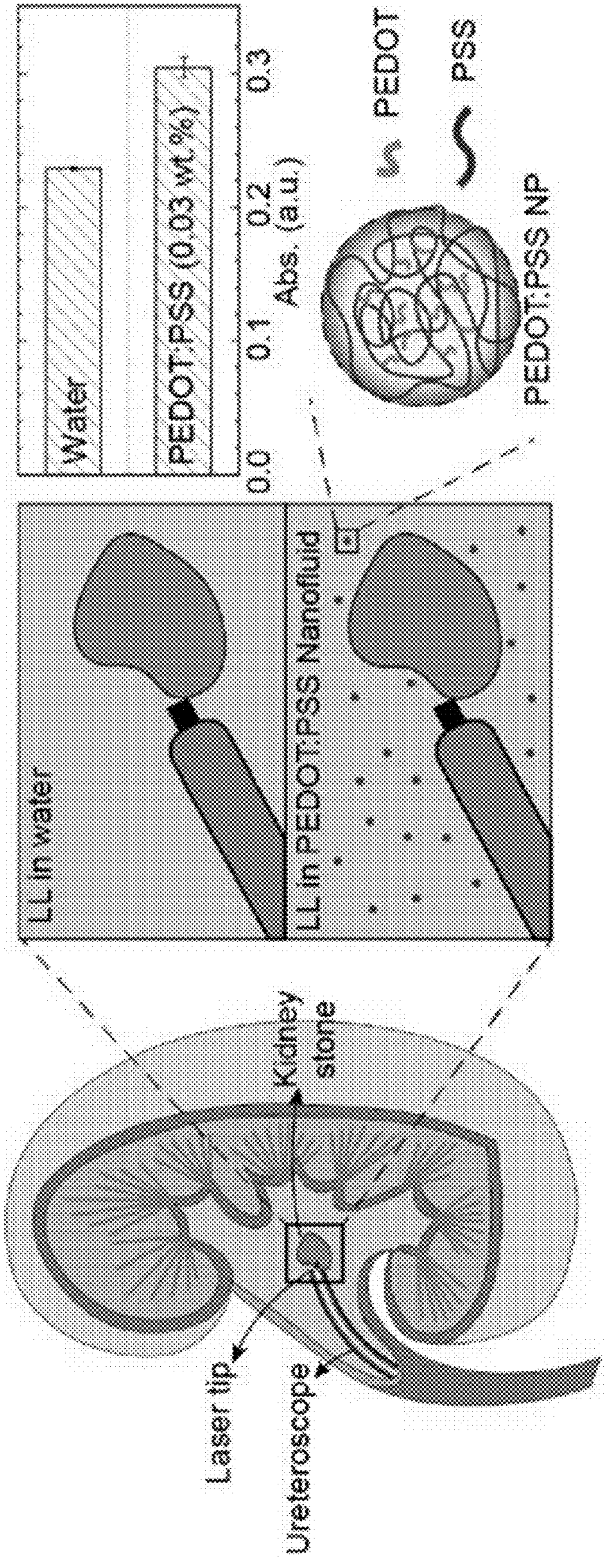
FIG. 1: Schematic illustration of LL in kidney stone removal. Traditional LL is conducted in saline (water) with a low absorption coefficient at 2120 nm. Introducing PEDOT: PSS nanofluid can enhance the stone damage efficiency by increasing the absorption coefficient.
Figure 2:
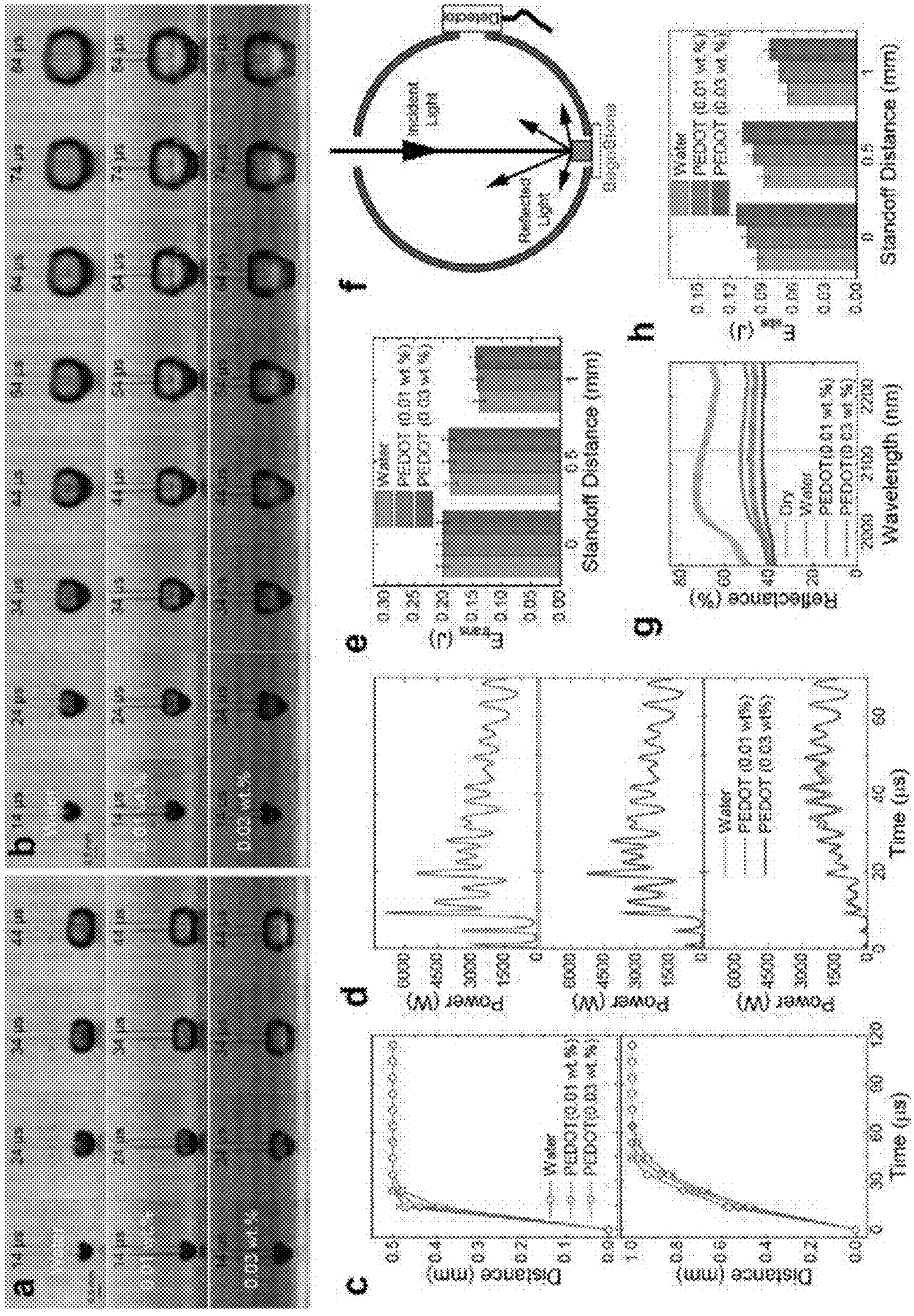
FIG. 2A-H: Bubble dynamics and calculated laser energies. (a, b) Snapshots of bubbles generation and expansion during one pulse of the LL in different fluids (from top to bottom: water, 0.01 wt. %, and 0.03 wt. % PEDOT: PSS nanofluid) with a glass slide placed at a distance of 0.5 mm (a) and 1 mm (b) in front of the laser fiber. (c) Temporal change of the distance between fiber and bubble front in various fluids (top:SD=0.5 mm, bottom:SD=1 mm. Error bars are standard deviations of 45 measurements). (d) The output power of the 60th pulse of the Ho:YAG laser (top) and calculated transmitted powers in different fluids (middle:SD=0.5 mm, bottom:SD=1 mm). (e) Calculated average transmitted energy at different SDs (Error bars are standard deviations of 45 measurements). (f) Scheme of NIR reflectance measurement of the soaked stones using an integrating sphere. (g) Measured NIR reflectance of stones. (h) Calculated energy absorbed by the stones soaked with various fluids.
Figure 8:
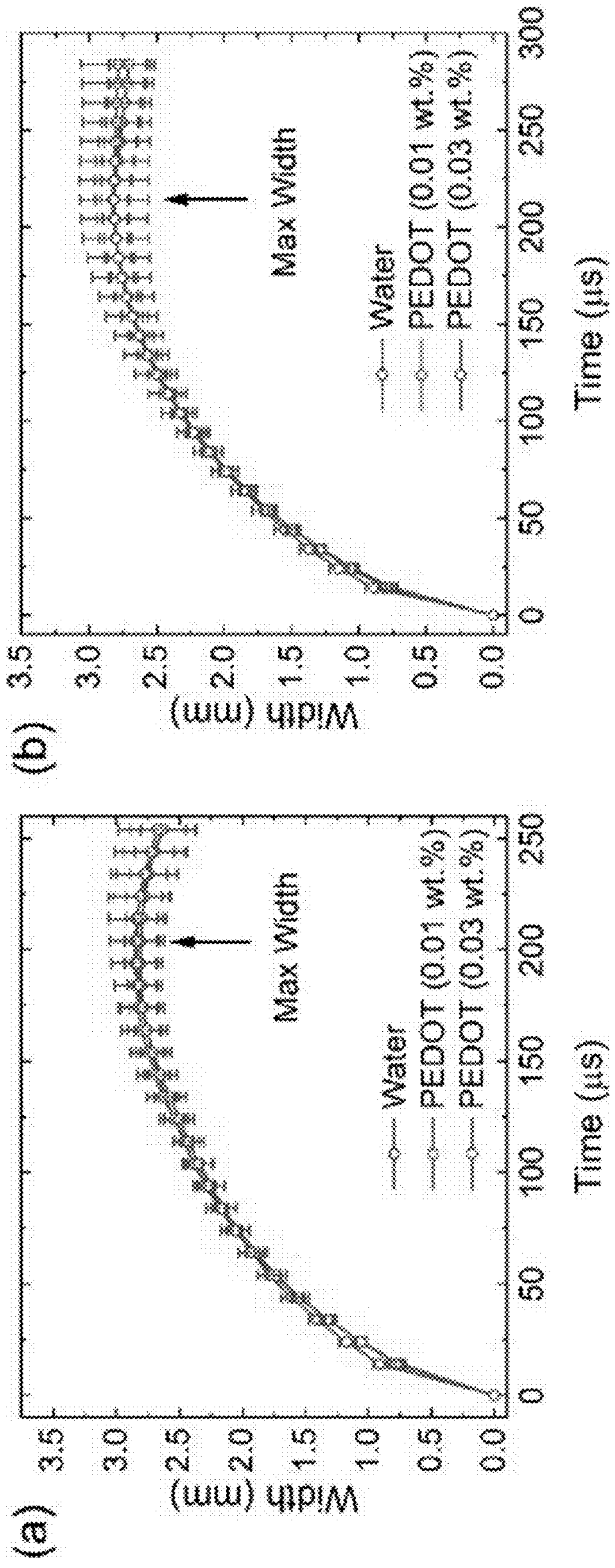

The impact of nanofluids on the Moses effect can be evaluated by measuring the size and expansion rate of bubbles in different concentrations using high-speed imaging operating at 100,000 frames per second. FIGS. 2(*a*) and 2(*b*) depict the initial frames of bubble generation and expansion in different PEDOT: PSS concentrations at SDs of 0.5 mm and 1 mm, respectively. To reproduce the laser-fluid-stone interaction during LL, a glass slide can be placed in front of the fiber at a certain distance. The width change of the bubbles in different fluids shows no significant difference in the maximum bubble width at each SD (FIG. 8). However, measurements of the distance between the fiber tip and the bubble front in each frame, summarized in FIG. 2(*c*), show that the bubble in 0.03 wt. % PEDOT: PSS nanofluid expands the fastest at both SDs. This can facilitate the removal of the ablated dust inside the crater and thus enhance the treatment efficiency. The transient transmittance of 2120 nm light can be calculated by considering the total optical density along the light path (FIG. 9). By multiplying the transient transmittance with the laser output power (FIG. 2(*d*), top), the transient transmitted powers at these SDs can be obtained (FIG. 2*d*, middle and bottom). Higher laser powers can be transmitted at the early stage of each pulse due to the faster establishment of the vapor tunnel in 0.03 wt. % PEDOT: PSS nanofluid.

The transmitted energy can be calculated by integrating the transmitted power over time. In FIG. 2(*e*), assuming that the laser energy of each pulse can be transmitted with no loss (0.2 J) at the SD of 0 mm, less laser energy is transmitted as the SD increases, with the energy loss primarily caused by fluid absorption in between. However, comparing the transmitted energies in PEDOT: PSS nanofluids to those in water at the same SD reveals an increasing trend. For example, there is a 4.8% increase in transmitted energy for 0.03 wt. % PEDOT: PSS compared to water (0.1449±0.0098 J vs. 0.1383±0.0092 J) at the SD of 1 mm. Similarly, this increase is 2.1% at the SD of 0.5 mm (0.1903±0.0109 J vs. 0.1864±0.0106 J).

Impact of Nanofluids on Stone Absorption

BegoStone and human kidney stones contain numerous submillimeter pores, allowing the surrounding fluid to percolate into the stone and occupy the small pores. Additionally, nanoparticles such as PEDOT: PSS can attach to the stone surface due to chemical or charge-induced adsorption. Both PEDOT: PSS NPs trapped in the pores and those attached to the stone's surface contribute to increased absorption of laser energy. As a result, even though the total transmitted energy is similar due to the similar bubble channeling time series, the nanofluid-modified stones receive more energy than stones in pure water. The NIR reflectance of BegoStones with various trapped fluids can be measured using a spectrometer equipped with an integrating sphere (FIG. 2(*f*)), with results summarized in FIG. 2(*g*). Stone reflectance at 2120 nm decreases from 52.9% to 43.2% when water is replaced with 0.03 wt. % PEDOT nanofluid. The absorbed energy, derived by considering both transmitted energy and BegoStone absorption when soaked with fluids. FIG. 2(*h*) shows a 20.6% (0.0942±0.0046 J vs. 0.1136±0.0056 J), 23.2% (0.0878±0.0049 J vs. 0.1082±0.0061 J), and 26.2% (0.0652±0.0043 J vs. 0.0823±0.0055 J) increase in absorbed energy in 0.03 wt. % PEDOT: PSS nanofluid compared to water, at SDs of 0, 0.5, and 1 mm, respectively.

In addition to the increased absorbed laser energy accounting for the enhanced photothermal ablation, micro-explosions of the trapped PEDOT: PSS nanofluid inside the stone contribute to the improved overall ablation efficiency.

Micro-explosion comprises fluid vaporization inside the stone pores that causes dramatic fracturing due to the high vapor pressure.

Similar faster bubble expansion behavior has been observed in experiments where surfactants were added to water to reduce its surface tension. Unlike surfactants with amphiphilic molecular structures, PEDOT: PSS NPs have a hydrophilic shell that enables their dispersity in water. Therefore, when these NPs are dispersed in water, they remain inside the water instead of at the water-air interface, resulting in no change to the surface tension. Surface tension measurements of PEDOT: PSS nanofluids with various concentrations (FIG. 10) show that within the investigated concentration range, the surface tension of the fluid remains constant and close to that of water. This finding demonstrates that the faster expansion of vapor bubbles in PEDOT: PSS nanofluid is due to its enhanced NIR absorbance.

Example 4: Cytotoxicity

PEDOT: PSS in various forms, including microwires, porous microparticles, films, and cell scaffolds, demonstrates good biocompatibility. Additionally, a PEDOT-based coating (Amplicoat, Heraeus Medical Components) is an FDA-approved material. The cytotoxicity of PEDOT: PSS NPs under relevant treatment conditions can be measured by incubating murine epithelial cells (mIMCD-3) with PEDOT: PSS nanofluids of increasing concentrations (0.006 wt. % to 0.1 wt. %) for various durations (1 hour or 24 hours). The cell viabilities from all experiments are summarized in FIG. 11. Cells incubated in 0.1 wt. % PEDOT: PSS nanofluid exhibit a decrease in cell viability after 1 hour incubation. The viability of the cells starts to decrease at a concentration higher than 0.05 wt. % for 24 hours incubation. Given the moderate concentration (0.03 wt. %) and the typical duration of LL treatment (~1 hour), the use of a PEDOT: PSS nanofluid in LL shows promise.

Temperature changes recorded during the stone damage experiment show an abrupt temperature rise when the laser is activated in all three fluids (water, 0.01 wt. %, and 0.03 wt. % PEDOT: PSS nanofluids, FIG. 12). Although the temperature rise is slightly higher in PEDOT: PSS nanofluids compared to water (water: 0.934° C., 0.01 wt. %: 1.134° C., 0.03 wt. %: 1.191° C.), such a temperature increase can be managed using irrigation flow. Furthermore, the significant ablation efficiency improvement using 0.03 wt. % PEDOT: PSS nanofluid can potentially reduce treatment duration, thereby reducing the risk of accumulated thermal injury and other surgical complexities.

Example 5: Improving Stone Ablation Efficiency of Laser Lithotripsy Using Indium Tin Oxide Nanofluid A previous study demonstrated that introducing conductive polymer nanoparticles (PEDOT: PSS) into the fluid surrounding a stone enhances laser energy absorption, increasing the stone ablation efficiency of laser lithotripsy (LL) with a Ho:YAG laser by 38% under optimized conditions. The strong visible-spectrum absorption of PEDOT: PSS nanoparticles limits its applicable concentration under clinically relevant conditions. For example, at a concentration of 0.03 wt. %, the fluid's absorbance to the Ho:YAG laser (2120 nm) increases by 33%. The mechanism suggests that LL efficiency increases proportionally with fluid absorbance, making nanomaterials with strong infrared absorption and minimal visible absorption advantageous.

Indium tin oxide nanoparticles (ITO NPs), which have absorption peaks in the infrared spectrum due to localized surface plasmon resonance, increase fluid absorbance to the Ho:YAG laser by 647% while maintaining a clear view under the ureteroscope. This results in a 118% enhancement in Ho:YAG LL ablation efficiency. Additionally, the ITO nanofluid improves ablation efficiency with Tm:YAG (2013 nm) and thulium fiber lasers (1940 nm), offering broader applicability and greater advantage over PEDOT: PSS nanofluid.

Figure 13:
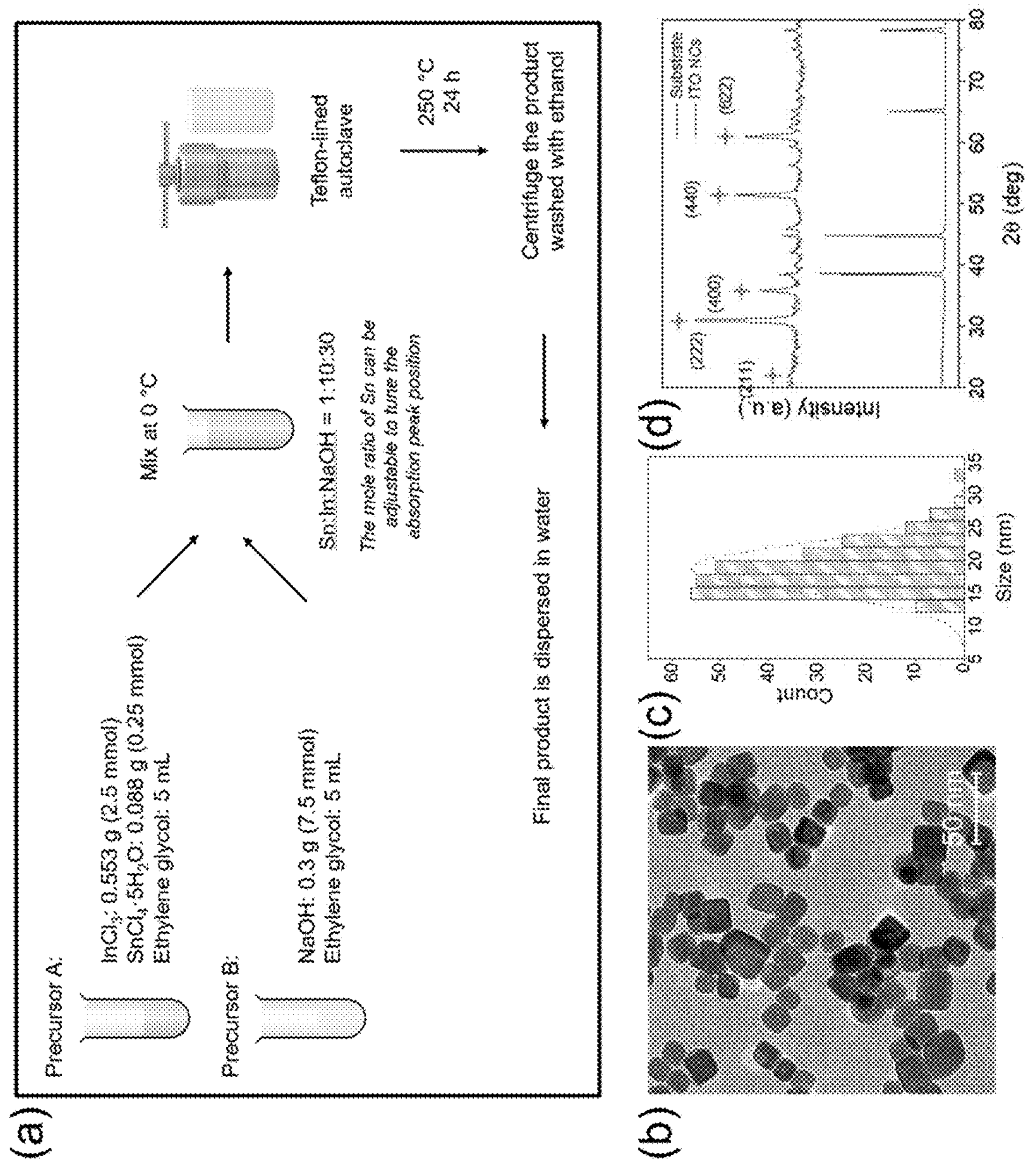

FIG. 13(*a*) illustrates the typical ITO NP synthesis procedure via a solvothermal reaction. After purification, the ITO NPs form a stable colloidal dispersion in water with a uniform average size of ~18 nm (FIGS. 13(*b*) and 13(*c*)). The X-ray diffraction pattern of the powdered product (FIG. 13(*d*)) confirms the ITO composition.

The ITO NP absorption peak can be tuned by adjusting the $SnCl_4/InCl_3$ feeding ratio. FIG. 14 shows that, with no $SnCl_4$ added, the dispersion appears milky white, with no significant absorption peak across the 400-2500 nm spectrum. Increasing the feeding ratio to 3.23% changes the dispersion color to light blue and results in a strong absorption peak at 2100 nm. The peak continues to shift to lower wavelengths as the ratio increases, but beyond 9.09%, the peak stops shifting and its intensity decreases significantly. This tunable absorption is explained by the localized surface plasmon resonance (LSPR) of free carriers in the ITO NPs; adding more $SnCl_4$ increases free carrier concentration, blue-shifting the LSPR peak. However, due to size mismatches, further Sn incorporation into the In203 lattice is limited.

ITO NPs synthesized with a 4.76% feeding ratio were selected for further characterization, as these had the highest absorbance at all three laser wavelengths (Ho:YAG: 2120 nm, Tm; YAG: 2013 nm and thulium fiber laser: 1940 nm) among the samples prepared. FIG. 15 compares the optical properties of ITO and PEDOT: PSS nanofluids. Both NPs enhance infrared fluid absorption significantly, but ITO NPs exhibit minimal visible light absorption, allowing high transparency at concentrations up to 1.0 wt. %. In contrast, PEDOT: PSS nanofluid allows visibility of background patterns only at concentrations below 0.03 wt. % (FIG. 15(*a*)). FIG. 15(*e*) shows that 0.5 wt. % ITO nanofluid achieves similar visible-spectrum transmittance (~50%) to 0.03 wt. % PEDOT: PSS nanofluid, yet with far greater absorption coefficients at all three laser wavelengths (FIG. 15(*f*): 147% vs. 6% at 1940 nm, 371% vs. 11% at 2013 nm, and 647% vs. 33% at 2120 nm).

The ITO nanofluids demonstrated good stability, with no precipitation after several weeks at room temperature. However, immersing the BegoStone in ITO nanofluid significantly increased ionic strength, reducing electrostatic repulsion among ITO NPs and causing rapid aggregation and precipitation within minutes (FIG. 16(*a*)). These large aggregates obstructed the ureteroscopic view (FIG. 16(*b*)). To enhance colloidal stability, polyacrylic acid (PAA) was grafted onto the ITO NP surface and coated with a ~3 nm $SiO_2$ shell using a sol-gel method. TEM images (FIG. 16(*c*)) show $SiO_2$ encapsulating ITO NPs. After coating, the zeta potential changed from positive to negative, and the hydrodynamic diameter increased from ~50 nm to ~80 nm due to the encapsulation. The $SiO_2$ shell improved stability against ionic strength, allowing clear visualization of the BegoStone in ITO@$SiO_2$ nanofluid at concentrations up to 0.5 wt. % (FIG. 16(*f*)).

The ablation efficiency improvement of 0.5 wt. % ITO@$SiO_2$ nanofluid for LL was evaluated using three lasers at two standoff distances (SD) in dusting mode (Ep=0.2 J, f=20 Hz, 60 pulses). FIG. 17(*a*) shows craters produced at the BegoStone surface, with larger craters observed in 0.5 wt. % ITO@$SiO_2$ nanofluid compared to water, regardless of laser type. Crater volumes in FIG. 17(*b*) measured by optical coherence tomography reveal a minimum ablation efficiency improvement of 118%, reaching over 200% under certain conditions.

The cytotoxicity of 0.25 wt. % ITO@$SiO_2$ nanofluid on mouse kidney cells was assessed over 1 and 24 hours (FIG. 18). The MTT assay showed no statistically significant changes in cell viability for either exposure, indicating high biocompatibility.

What is claimed is:

1. A method of performing laser lithotripsy, the method comprising:

introducing a lithotripsy medium comprising nanoparticles into a body cavity of a subject, wherein the body cavity of the subject comprises one or more target obstructions; and applying laser energy through the lithotripsy medium to disrupt the one or more target obstructions;

wherein the nanoparticles have a diameter configured to enhance absorption efficiency of the laser energy.

2. The method of claim 1, wherein the laser energy comprises a wavelength configured to enhance absorption efficiency of the laser energy by the lithotripsy medium.

3. The method of claim 2, wherein the wavelength of the laser energy is from about 750 nm to about 2500 nm.

4. The method of claim 1, wherein the diameter of the nanoparticles is from about 1 nm to about 250 nm.

5. The method of claim 1, wherein the nanoparticles are present in the lithotripsy medium at a concentration from about 0.001 wt. % to about 10 wt. %.

6. The method of claim 1, wherein the nanoparticles are comprised of at least one organic polymer.

7. The method of claim 6, wherein the at least one organic polymer comprises poly(3,4-ethylenedioxythiophene) polystyrene sulfonate (PEDOT: PSS).

8. The method of claim 7, wherein the wavelength of the laser energy is from about 1800 nm to about 2200 nm.

9. The method of claim 7, wherein the diameter of the nanoparticles is from about 50 nm to about 250 nm.

10. The method of claim 7, wherein the nanoparticles are present in the lithotripsy medium at a concentration from about 0.006 wt. % to about 0.03 wt. %.

11. The method of claim 7, wherein the laser energy is applied using a holmium laser.

12. The method of claim 1, wherein the nanoparticles are comprised of at least one inorganic compound.

13. The method of claim 12, wherein the at least one inorganic compound comprises indium tin oxide.

14. The method of claim 13, wherein the wavelength of the laser energy is from about 1800 nm to about 2200 nm.

15. The method of claim 13, wherein the diameter of the nanoparticles is from about 1 nm to about 100 nm.

16. The method of claim 13, wherein the nanoparticles are present in the lithotripsy medium at a concentration from about 0.1 wt. % to about 1 wt. %.

17. The method of claim 13, wherein the laser energy is applied using a thulium laser.

18. The method of claim 1, wherein applying the laser energy comprises generating vapor bubbles in the lithotripsy medium between a laser fiber tip and the one or more target obstructions.

19. The method of claim 1, wherein the one or more target obstructions comprise kidney stones.

20. The method of claim 1, further comprising:

providing at least a second lithotripsy medium comprising nanoparticles having a different diameter than the nanoparticles in the first lithotripsy medium; and alternating between the first and second lithotripsy mediums during the laser lithotripsy procedure to modify light absorption characteristics and/or efficiency.

21. The method of claim 20, wherein the first lithotripsy medium provides enhanced absorption efficiency at a first wavelength and the second lithotripsy medium provides enhanced absorption efficiency at a second wavelength.

22. A system for performing laser lithotripsy, comprising:

a laser source configured to generate laser energy;

a fluid delivery component configured to deliver a lithotripsy medium comprising nanoparticles having a diameter selected to enhance absorption efficiency at the wavelength of the laser energy; and an optical fiber configured to deliver the laser energy to one or more target obstructions through the lithotripsy medium.

23. The system of claim 22, wherein the laser energy comprises a wavelength configured to enhance absorption efficiency of the laser energy by the lithotripsy medium.

24. The system of claim 23, wherein the wavelength of the laser energy is from about 750 nm to about 2500 nm.

25. The system of claim 22, wherein the diameter of the nanoparticles is from about 1 nm to about 250 nm.

26. The system of claim 22, wherein the nanoparticles are present in the lithotripsy medium at a concentration from about 0.001 wt. % to about 10 wt. %.

27. The system of claim 22, wherein the nanoparticles are comprised of at least one organic polymer.

28. The system of claim 27, wherein the at least one organic polymer comprises poly(3,4-ethylenedioxythiophene) polystyrene sulfonate (PEDOT: PSS).

29. The system of claim 28, wherein the wavelength of the laser energy is from about 1800 nm to about 2200 nm.

30. The system of claim 28, wherein the diameter of the nanoparticles is from about 50 nm to about 250 nm.

31. The system, of claim 28, wherein the nanoparticles are present in the lithotripsy medium at a concentration from about 0.006 wt. % to about 0.03 wt. %.

32. The system of claim 28, wherein the laser source is a holmium laser.

33. The system of claim 22, wherein the nanoparticles are comprised of at least one inorganic compound.

34. The system of claim 33, wherein the at least one inorganic compound comprises indium tin oxide.

35. The system of claim 34, wherein the wavelength of the laser energy is from about 1800 nm to about 2200 nm.

36. The system of claim 34, wherein the diameter of the nanoparticles is from about 1 nm to about 100 nm.

37. The system of claim 34, wherein the nanoparticles are present in the lithotripsy medium at a concentration from about 0.1 wt. % to about 1 wt. %.

38. The system of claim 34, wherein the laser source is a thulium laser.

39. The system of claim 22, wherein the fluid delivery component is configured to deliver a second lithotripsy medium comprising nanoparticles having a second diameter selected to modify light absorption characteristics and/or efficiency.

40. A method of manufacturing a lithotripsy medium, comprising: selecting a target wavelength for enhanced absorption of laser energy; synthesizing nanoparticles having a diameter selected to provide an absorption peak at the target wavelength; and dispersing the nanoparticles in the lithotripsy medium at a selected concentration.

* * * * *